(12) United States Patent
Allen et al.

(10) Patent No.: US 7,867,699 B2
(45) Date of Patent: Jan. 11, 2011

(54) METHOD OF SYNTHESIZING AND PURIFYING DKK PROTEINS AND DKK PROTEINS OBTAINED THEREBY

(75) Inventors: Kristina Allen, Hopkinton, MA (US); Anthony Anisowicz, West Newton, MA (US); Wei Chen, Acton, MA (US); Girija Krishnamurthy, Chestnut Ridge, NY (US); Matthew Olson, Spring City, PA (US)

(73) Assignees: Wyeth, Madison, NJ (US); Oscient Pharmaceuticals Corporation, Waltham, MA (US)

( * ) Notice: Subject to any disclaimer, the term of this patent is extended or adjusted under 35 U.S.C. 154(b) by 388 days.

(21) Appl. No.: 10/593,089

(22) PCT Filed: Mar. 23, 2005

(86) PCT No.: PCT/US2005/010001

§ 371 (c)(1),
(2), (4) Date: Sep. 10, 2007

(87) PCT Pub. No.: WO2005/095448

PCT Pub. Date: Oct. 13, 2005

(65) Prior Publication Data

US 2008/0038775 A1 Feb. 14, 2008

Related U.S. Application Data

(60) Provisional application No. 60/555,406, filed on Mar. 23, 2004.

(51) Int. Cl.
*A01N 1/02* (2006.01)
*C07K 1/00* (2006.01)

(52) U.S. Cl. .......................................... 435/2; 530/350

(58) Field of Classification Search .................. 530/350; 435/2
See application file for complete search history.

(56) References Cited

U.S. PATENT DOCUMENTS

| | | | |
|---|---|---|---|
| 6,344,541 B1 | 2/2002 | Bass et al. | 530/324 |
| 6,844,422 B1 | 1/2005 | Niehrs et al. | 530/350 |
| 6,962,797 B2 | 11/2005 | Goddard et al. | 435/69.1 |
| 7,057,017 B2 | 6/2006 | McCarthy | 530/350 |
| 7,446,181 B2 * | 11/2008 | McCarthy | 530/388.23 |

FOREIGN PATENT DOCUMENTS

| | | |
|---|---|---|
| WO | 98/46755 | 10/1998 |
| WO | 99/46281 | 9/1999 |
| WO | 02/066509 | 8/2002 |

OTHER PUBLICATIONS

Shou Jiang et al. "Human Dkk-1, a gene' encoding a Wnt antagonist, responds to DNA damage and its overexpression sensitizes brain tumor cells to apoptosis following alkylation damage of DNA." *Oncogene*, vol. 21, No. 6, Jan. 31, 2002, pp. 878-889.

Glinka et al. "Dickkopf-1 is a member of a new family of secreted proteins and function in head induction." *Nature*, vol. 391, No. 6665, Jan. 22, 1998, pp. 357-362.

Fedi et al. "Isolation and Biochemical Characterization of the Human Dkk-1 Homologue, a Novel Inhibitor of Mammalian Wnt Signaling." *The Journal of Biological Chemistry*, vol. 274, No. 27, Jul. 2, 1999, pp. 19465-19472.

* cited by examiner

*Primary Examiner*—Maryam Monshipouri
(74) *Attorney, Agent, or Firm*—Drinker Biddle & Reath LLP

(57) ABSTRACT

The invention relates to a novel method of inexpensively synthesizing large quantities of an essentially pure, biologically active, glycosylated Dkk protein, including mammalian and human Dkk proteins (e.g., human Dkk1). The invention further relates to the synthetically produced essentially purified, glycosylated and biologically active Dkk protein, and the characteristics of the protein.

20 Claims, 17 Drawing Sheets

ATGATGGCTCTGGGCGCAGCGGGAGCTACCCGGGTCTTTGTCGCGATGGTAGCGGCGGCTC
TCGGCGGCCACCCTCTGCTGGGAGTGAGCGCCACCTTGAACTCGGTTCTCAATTCCAACGC
TATCAAGAACCTGCCCCCACCGCTGGGCGGCGCTGCGGGGCACCCAGGCTCTGCAGTCAGC
GCCGCGCCGGGAATCCTGTACCCGGGCGGGAATAAGTACCAGACCATTGACAACTACCAGC
CGTACCCGTGCGCAGAGGACGAGGAGTGCGGCACTGATGAGTACTGCGCTAGTCCCACCCG
CGGAGGGGACGCGGGCGTGCAAATCTGTCTCGCCTGCAGGAAGCGCCGAAAACGCTGCATG
CGTCACGCTATGTGCTGCCCCGGGAATTACTGCAAAAATGGAATATGTGTGTCTTCTGATC
AAAATCATTTCCGAGGAGAAATTGAGGAAACCATCACTGAAAGCTTTGGTAATGATCATAG
CACCTTGGATGGGTATTCCAGAAGAACCACCTTGTCTTCAAAAATGTATCACACCAAAGGA
CAAGAAGGTTCTGTTTGTCTCCGGTCATCAGACTGTGCCTCAGGATTGTGTTGTGCTAGAC
ACTTCTGGTCCAAGATCTGTAAACCTGTCCTGAAAGAAGGTCAAGTGTGTACCAAGCATAG
GAGAAAAGGCTCTCATGGACTAGAAATATTCCAGCGTTGTTACTGTGGAGAAGGTCTGTCT
TGCCGGATACAGAAAGATCACCATCAAGCCAGTAATTCTTCTAGGCTTCACACTTGTCAGA
GACACTCTAGAGGGCCCTTC*GAACAAAAACTCATCTCAGAAGAGGATCTG*AATATGCATAC
CGGT<u>CATCATCACCATCACCAT</u>TGA

FIG. 15A

<u>MMALGAAGATRVFVAMVAAALGGHPLLGVSATLNSVLNSNAIKNLPPPLGGAAGHPGSAVS</u>
AAPGILYPGGNKYQTIDNYQPYPCAEDEECGTDEYCASPTRGGDAGVQICLACRKRRKRCM
RHAMCCPGNYCKNGICVSSDQNHFRGEIEETITESFGNDHSTLDGYSRRTTLSSKMYHTKG
QEGSVCLRSSDCASGLCCARHFWSKICKPVLKEGQVCTKHRRKGSHGLEIFQRCYCGEGLS
CRIQKDHHQASNSSRLHTCQRHSRGPF*EQKLISEEDL*NMHTG<u>HHHHHH</u>

FIG. 15B

SEQUENCE LISTING

<160> NUMBER OF SEQ ID NOS: 5

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1 tttttttggat ccgccaccat gatggctctg ggcgcag                              37

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttttttcta gagtgtctct gacaagtgtg                                        30

<210> SEQ ID NO 3
<211> LENGTH: 21
<212> TYPE: PRT
<213> ORGANISM: Homo sapiens

<400> SEQUENCE: 3

Arg Ile Gln Lys Asp His His Gln Ala Ser Asn Ser Ser Arg Leu His
 1               5                  10                  15

Thr Cys Gln Arg His
            20

<210> SEQ ID NO 4
<211> LENGTH: 879
<212> TYPE: DNA
<213> ORGANISM: Homo sapiens

<400> SEQUENCE: 4
atgatggctc tgggcgcagc gggagctacc cgggtctttg tcgcgatggt agcggcggct        60
ctcggcggcc accctctgct gggagtgagc gccaccttga actcggttct caattccaac      120
gctatcaaga acctgccccc accgctgggc ggcgctgcgg gcacccagg ctctgcagtc       180 agcgccgcgc cgggaatcct gtaccggggc gggaataagt accagaccat tgacaactac      240
cagccgtacc cgtgcgcaga ggacgaggag tgcggcactg atgagtactg cgctagtccc      300
acccgcggag gggacgcggg cgtgcaaatc tgtctcgcct gcaggaagcg ccgaaaacgc      360
tgcatgcgtc acgctatgtg ctgccccggg aattactgca aaatggaat atgtgtgtct      420 tctgatcaaa atcatttccg aggagaaatt gaggaaacca tcactgaaag ctttggtaat      480
gatcatagca ccttggatgg gtattccaga agaaccacct tgtcttcaaa aatgtatcac      540
accaaaggac aagaaggttc tgtttgtctc cggtcatcag actgtgcctc aggattgtgt      600
tgtgctagac acttctggtc caagatctgt aaacctgtcc tgaaagaagg tcaagtgtgt      660
accaagcata ggagaaaagg ctctcatgga ctagaaatat ccagcgttg ttactgtgga      720 gaaggtctgt cttgccggat acagaaagat caccatcaag ccagtaattc ttctaggctt      780
cacacttgtc agagacactc tagagggccc ttcgaacaaa aactcatctc agaagaggat      840

```
ctgaatatgc ataccggtca tcatcaccat caccattga                             879

<210> SEQ ID NO 5
<211> LENGTH: 292
<212> TYPE: PRT
<213> ORGANISM: Homo sapiens

<400> SEQUENCE: 5

Met Met Ala Leu Gly Ala Ala Gly Ala Thr Arg Val Phe Val Ala Met
 1               5                  10                  15

Val Ala Ala Ala Leu Gly Gly His Pro Leu Leu Gly Val Ser Ala Thr
                20                  25                  30

Leu Asn Ser Val Leu Asn Ser Asn Ala Ile Lys Asn Leu Pro Pro Pro
            35                  40                  45

Leu Gly Gly Ala Ala Gly His Pro Gly Ser Ala Val Ser Ala Ala Pro
    50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Lys Arg Cys Met Arg His Ala Met Cys Cys
        115                 120                 125

Pro Gly Asn Tyr Cys Lys Asn Gly Ile Cys Val Ser Ser Asp Gln Asn
    130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
    210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His Ser Arg Gly Pro Phe Glu
            260                 265                 270

Gln Lys Leu Ile Ser Glu Glu Asp Leu Asn Met His Thr Gly His His
        275                 280                 285

His His His His
    290
```

METHOD OF SYNTHESIZING AND PURIFYING DKK PROTEINS AND DKK PROTEINS OBTAINED THEREBY

This application is a 371 filing of PCT application no. PCT/US2005/010001 filed on Mar. 23, 2005, which claims priority to U.S. Patent application No. 60/555,406 filed on Mar. 23, 2004.

REFERENCE TO A SEQUENCE LISTING

A Sequence Listing containing SEQ ID NOS: 1-5 is incorporated herein by reference.

FIELD OF THE INVENTION

Methods of recombinantly synthesizing and purifying mammalian Dkk proteins, preferably mammalian Dkk1, are disclosed along with the proteins produced thereby, and the characteristics of the proteins.

BACKGROUND OF THE INVENTION

The Dkk1 gene, also called Dickkopf-1 (German for "big head" and "stubborn"), is a prototype member of a gene family that encodes secreted glycoproteins. These proteins control cell fate and neural patterning during embryonic development. The other Dkk family members include Dkk-2, Dkk-3 and Dkk-4. All four Dkk proteins are secreted and are synthesized as precursor proteins with an N-terminal signal peptide and two conserved cysteine-rich domains, which are separated by a linker region.

Evidence has been presented showing that Dkk1 functions as a potent inhibitor of the Wnt signaling pathway, a pathway that enables appropriate positioning and development of the embryonic brain and other organ structures (Shou et al., 2002 *Oncogene* 21: 878-889). Dkk-4 functions as another Wnt antagonist. Dkk-3 has not been demonstrated to affect Wnt signaling, and Dkk-2 acts as both an antagonist and an agonist of Wnt signaling, depending on the cellular context in which it is found.

The Wnt pathway consists of many highly conserved Wnt protein ligands that bind to the Frizzled family of receptors and trigger a cytoplasmic signal transduction cascade in which glycogen synthase kinase-3 (GSK-3) and β-catenin play essential roles. In the absence of Wnt signaling, β-catenin is associated with a cytoplasmic complex containing GSK-3, axin and the adenomatous polyposis coli protein (APC). In this complex, GSK-3 constitutively phosphorylates β-catenin. The phosphorylation of β-catenin permits it to become ubiquinated. The ubiquitin moiety marks the protein for subsequent degradation. In the presence of Wnt signaling, GSK-3 is inactivated, leading to free and unphosphorylated β-catenin building up in the cytoplasm. This β-catenin pool then translocates to the nucleus, where it associates with members of the lymphocyte enhancer factor (LEF)/TCF family of transcription factors to activate a variety of target genes involved in growth, development and oncogenesis.

Some of the Wnt target genes include cyclin D1, engrailed-2, cyclooxygenase-2, c-myc, and numerous metalloproteinases. The homeostasis of the Wnt pathway is maintained in part by Wnt antagonists and agonists. Thus, the role of Dkk1, a Wnt antagonist, would serve to diminish the accumulation of free β-catenin. The balance of β-catenin pools in the cytoplasm and in the nucleus determines "in part", the outcome of Wnt signaling (Shou et al., 2002). The Dkk proteins (especially Dkk1) therefore play an active role in Wnt signaling. Dkk1 has been shown to be a target for the p53 tumor suppressor (Shou et al., 2002).

Therefore, adequate amounts of research grade Dkk1 or other Dkk proteins are needed for further study of p53 and Wnt signaling and their relationship to cancer and development.

Dkk1 has been produced via transient transfections with culture media being used as the protein is released into the culture media. Commercial vendors of Dkk1 also exist, such as R&D Systems (Minneapolis, Minn.). However, the commercially available forms of Dkk1 are in small quantities and costly (10 µg/$ 300); the commercially available forms also may not be functional depending on the assay used, if at all. Additionally, the commercially available form of Dkk1, as well as other forms taught in the literature, are either produced in low quantities, at high cost, were never purified, have reduced or altered biological activities or a combination of these flaws. Accordingly, new methods are needed for producing a Dkk1 protein with similar biological activity to the native form, in large quantities that was not costly. More particularly, there is a need to produce large quantities of Dkk, preferably Dkk1, to be used in high throughput screening (HTS) assays. This Dkk1 must be glycosylated in a pattern similar to the Dkk1 protein found in the host organism from which that Dkk1 derives. The loss of the glycosyl groups can significantly impact the activity of the protein in various assay systems.

SUMMARY OF THE INVENTION

Therefore, notwithstanding what has previously been reported in the literature, there exists a need for improved methods of preparing an isolated, glycosylated form of a Dkk protein which maintains biological activity after purification. Accordingly one aspect of the invention provides for a method of synthesizing a mammalian, essentially pure, glycosylated Dkk protein comprising the steps of:

(a) Preferably over-expressing a protein with the appropriate signal sequence that allows secretion of the Dkk protein into the media or extracellular space.

(b) harvesting culture media from a mammalian cell line with a nucleic acid encoding a mammalian Dkk protein in a replicating vector that synthesizes Dkk protein;

(c) purifying the filtered culture media across an affinity gradient column;

(d) collecting Dkk protein containing fractions from the column;

(e) concentrating the Dkk protein containing fractions in a phosphate buffered saline in the presence of a detergent and EDTA to produce a concentrated, mammalian, essentially pure, glycosylated Dkk protein. The method may further comprise a step for treating the culture media with one or more protease inhibitors and/or filtering the culture media prior to purifying the culture media. It is further contemplated that the treating step is additionally performed in the presence of a salt and imidazole. The salt can be NaCl, LiCl, or KCl, and can be in a final concentration of about 100 mM to about 1 M; the imidazole is present in a final concentration of about 0.5 mM to about 50 mM imidazole. More preferably the salt is present at about 500 mM, and the imidazole is present at a final concentration of about 5 mM.

A preferred aspect of this method contemplates the use of a detergent such as Tween, CHAPS, octylglucoside, Triton X, or NP-40. Another aspect of the invention provides for the use a metal (e.g., nickel, zinc or iron) affinity column as the affinity column.

In yet another aspect of the invention, the invention contemplates that the detergent is Tween-20 in the amount of about 0.01% to about 1% Tween-20 and EDTA is present in the amount of about 0.01 mM to about 2 mM EDTA. The Tween-20 may also be present in the amount of about 0.1% and the EDTA is present in the amount of about 0.5 mM EDTA. The Tween-20 may also be substituted for N-b-octyl-glucopyranoside in the amount of about 0.07 to 0.7% and EDTA is present at 0.5 mM. The Tween-20 may also be substituted for N-octyl-β-D-glycoside in the amount of about 0.05% to about 0.7% and EDTA is present in the amount of about 0.5 mM. EGTA may be substituted in the alternative for EDTA. The amount of EGTA used for EDTA would be equivalent (about 0.5 mM EGTA as discussed in this instance).

Yet a further aspect of the method contemplates the step of lyophilizing the essentially purified Dkk protein.

Another aspect of the invention contemplates that the Dkk protein being produced is Dkk1. Preferably, the Dkk1 is mammalian Dkk1 and more preferably human Dkk1.

Another aspect of the invention contemplates that the method uses an imidazole affinity gradient of about a 5 to about a 1,500 mM imidazole in a metal column and wherein the Dkk protein is tagged with histidine. More preferably, the imidazole gradient is about a 20 mM to about a 1,000 mM imidazole gradient.

The cells which may be used to produce the Dkk protein can be any transfectable cell line, preferably a transfectable mammalian cell line. A preferred cell line is HEK293T cells. Additional cell lines that can be utilized are discussed infra.

Another aspect of the invention contemplates a purified, glycosylated Dkk protein produced by the above methods. A preferred Dkk protein is Dkk1, preferably a mammalian Dkk1 and more preferably human Dkk1. The purified Dkk protein may have a selectable tag such as His or c-myc. Such a tag preferably is cleavable form the protein after purification of the protein. Thus, another aspect of the invention contemplates a proteolytic cleavage site between the selectable tag and the Dkk protein.

Another aspect of the invention contemplates a purified glycosylated, mammalian Dkk1 protein having at least one of the following properties:

(a) a protein purified to ≧95% homogeneity;

(b) a molecular weight of approximately 40 kD±2.0 kD as determined by SDS-PAGE;

(c) inhibition of Wnt3A activity; and (d) co-immunoprecipitation of a LRP5 protein or a fragment thereof comprising the ligand binding domain. Preferably the Dkk1 protein is human Dkk1.

Another aspect of the invention describes methods to determine the molar mass and the oligomeric state of Dkk1 in solution under non-denaturing conditions using analytical ultracentrifugation, SEC-MALLS, and electrospray mass spectroscopy methods and thermal stability by spectroscopic methods such as CD and fluorescence as a function of the concentration of Dkk1 having one or more of the following solution properties:

(i) weight average molar mass of Dkk1 ranges from about 32-kD to about 40-kD of the monomer or about 66-kD to about 77-kD of the homodimer, and any other equilibria that may exist between these species as determined by SEC-MALLS or AUC.

(ii) conformational and chemical heterogeneity due to differences in the extent of glycosylation of Dkk1 as determined by SEC-MALLS or ESI mass spectrometry;

(iii) conformational changes or changes in molar mass of Dkk1 when complexed with any natural ligand such as LRP5 as determined by AUC and SEC-MALLS;

(iv) elution profile of Dkk1 in a liquid chromatographic system using the estimated extinction coefficient of the protein of 19,610 M-1 cm-1 from the primary protein sequence and the refractive index changes (dn/dc) of about 0.186 for the unmodified protein, and a dn/dc value of about 0.130 to about 0.180 of Dkk1 protein that has been modified due to post-translational glycosylation as determined using an in-line HPLC refractometer;

(v) ability of Dkk1 to bind to a natural ligand, LRP5 with a definitive binding stoichiometry of 1:1 with respect to the polypeptide chains, which is determined using the increase in weight averaged molar mass relative to uncomplexed Dkk1 as determined by SEC-MALLS and increase in Z-averaged molar mass of free Dkk1 as determined by AUC (Sed-Vel);

(vi) distinct thermal unfolding transition of Dkk1 by CD or fluorescence spectroscopy and the stabilization of the unfolding transitions as evidenced by a measurable increase in $T_m$ of >2° C. in the presence of the natural ligand LRP5, which is distinct from the transitions of Dkk1 and LRP5 alone in the free state; and (vii) fluorescence emission spectra of the aromatic residues of Dkk1 such as tyrosine or tryptophan, between about 320 nm and about 350 nm; and (viii) CD absorption due to peptide backbone that is consistent with the folded conformational state consisting of one or more of the following: beta turns/sheet, alpha and 3/10 helix, extended beta strand, and other structures with an overall composition of 100% and the percentage of each of these structures ranging from 10% to about 100% within the protein.

BRIEF DESCRIPTION OF THE FIGURES

FIG. 15. Nucleic acid (A) and amino acid (B) sequences of human Dkk1 as used to obtain purified Dkk1 from the HEK293 EBNA cells infra. Open reading frames (ORF) are in bold in FIG. 15A. The secretion signal peptide of Dkk1 is in bold and underlined in FIG. 15B. The c-myc tag is in italics and underlined and $His_6$-tag is double underlined in FIG. 15A.

DETAILED DESCRIPTION OF THE INVENTION

1. Definitions and Acronyms

Figure 1:
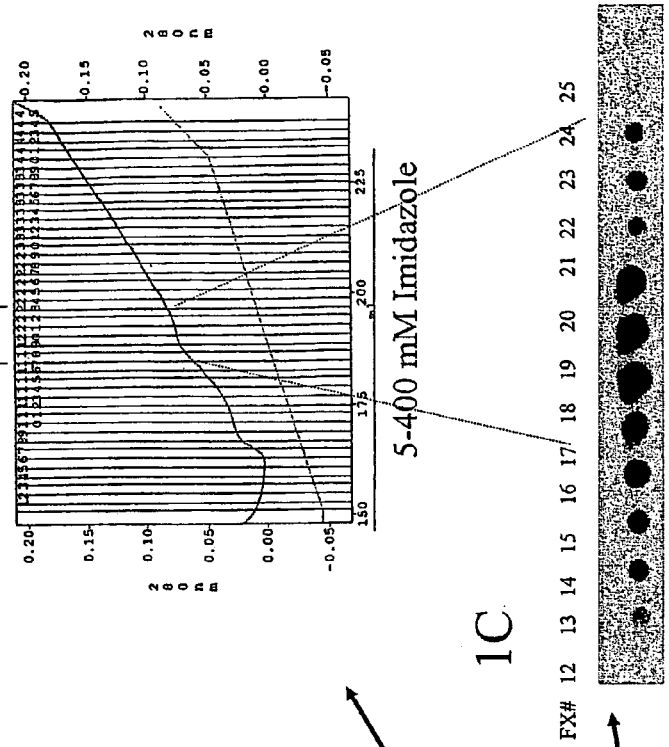
FIG. 1 Overview of the Dkk1 protein purification process. Panel 1A presents a flowchart of the process from collection of the culture media ("CM") through testing the purity and protein concentration. Panel 1B depicts the results obtained using a Ni column and the profile thereby obtained. Panel 1C presents a dot-blot of fractions 12-25 from the Ni Column to identify those fractions containing Dkk1. In this particular purification experiment, fractions 17-23 were pooled and used for subsequent experiments.

Unless defined otherwise, the scientific and technological terms and nomenclature used herein have the same meaning as commonly understood by a person of ordinary skill to which this invention pertains. The procedures for cell culture, transfections, molecular biology methods and the like are common methods used in the art. Such standard techniques can be found in reference manuals such as SAMBROOK ET AL., MOLECULAR CLONING: A LABORATORY MANUAL (Cold Spring Harbor Laboratory Press, 1989), AUSUBEL ET AL., CURRENT PROTOCOLS IN MOLECULAR BIOLOGY (Wiley, New York, 1994), as well as any of the other references cited herein.

Numeric ranges provided herein are meant to include any integer value within the range, unless otherwise indicated.

Nucleotide and polypeptide sequences presented herein are by single strand in the 5' to 3' or amino terminus to carboxy terminus orientation respectively. The one-letter nucleotide or amino acid symbols are those commonly used in the art.

1.1 Definitions

By "Dkk" is meant to include all members of the Dkk family of proteins (e.g., Dkk1, Dkk-2, Dkk-3 and Dkk-4) as well as soggy (Fedi et al., 1999, *J. Biol. Chem.* 274: 19465-72 and Krupnick et al., 1999 *Gene* 238: 301-313). Preferably, the Dkk is Dkk1. Preferably, the Dkk proteins are mammalian Dkk proteins and more preferably primate Dkk proteins, such as a human Dkk protein.

By "Dkk1" is meant to include all mammalian forms of Dkk1, and preferably human Dkk1 ("hDkk1"). Preferably, it is a full-length recombinant Dkk1 protein, but it can also include biologically active Dkk1 fragments (e.g., an example of biological activity of such a fragment would include regulation of the Wnt pathway). Additionally, the full length protein may further comprise a second polypeptide sequence in the form of a fusion protein. As used herein, Dkk1 is meant to include proteins from any species having a Wnt pathway in which Dkk1 interacts. Particularly preferred are mammalian species (e.g., murine, caprine, canine, bovine, feline, equine, primate, ovine, porcine and the like), with particularly preferred mammals being humans. Nucleic acid sequences encoding Dkk1 include, but are not limited to human Dkk1 (GenBank Accession Nos. AH009834, XM_005730, AF261158, AF261157, AF177394, AF127563 and NM_012242), *Mus nusculutis* dickkopf homolog 1 (GenBank Accession No. NM_010051), and *Danio rerio* dickkopf-1 (GenBank Accession Nos. AF116852 and AB023488). The genomic sequences with exon annotation are GenBank Accession Nos. AF261157 and AF261158. Also contemplated are homologs of these sequences which have Dkk1 activity in the Wnt pathway. Dkk1 amino acid sequences include, but are not limited to human dickkopf homolog 1 (GenBank Accession Nos. AAG15544, BAA34651, NP_036374, AAF02674, AAD21087, and XP_005730), *Danio rerio* (zebrafish) dickkopf1 (GenBank Accession Nos. BAA82135 and AAD22461) and murine dickkopf-1 (GenBank Accession Nos. O54908 and NP_034181). Variants and homologs of these sequences which possess Dkk1 activity are also included when referring to Dkk1.

By "synthesized Dkk" is meant a Dkk protein in the Dkk family of proteins produced either synthetically (i.e., chemically) or recombinantly. Again, the Dkk protein preferably is either a full-length recombinant protein or a biologically active fragment of a Dkk protein (e.g., an example of biological activity of such a fragment would include regulation of the Wnt pathway or other protein ligand).

By "purified" is meant a protein that is about 40% or more Dkk protein. Preferably, the protein is about 50 to about 95% or more pure (or every integer value within that range).

By "mammal" and "mammalian" is meant to include, but is not limited to, rodents (e.g., mice, rats, hamsters, guinea pigs, chinchilla and the like), canines, felines, ovines, bovines, porcines, camelids, equines, domesticated cloven animals (e.g., goats, donkeys, llama, sheep and the like), and primates (especially human). Other species that express Dkk include *Drosophila, Xenopus* and *C. elegans*, which can be used as model systems to test Dkk activity. Accordingly, Dkk from all animal species are contemplated herein.

As used herein, the expressions "host cell", "cell," "cell line," and "cell culture" are used interchangeably and all such designations include progeny. Thus, the words "transformants", "transformed cells" and "transfected cells" include the primary subject cell and cultures derived therefrom without regard for the number of transfers. It is also understood that all progeny may not be precisely identical in DNA content and other biological characteristics, due to deliberate or inadvertent mutations. Such mutant progeny cells, which secrete a recombinant Dkk protein that have the same biological activity and/or characteristics as the Dkk1 produced from the parent cells, are also included by these terms. Where distinct designations are intended, it will be clear from the context. These cells are preferably mammalian host cells.

By "vector" or "expression vector" is meant a replicating system comprising such cassettes as transcription and translation cassettes or marker genes so that the protein of interest (i.e., a Dkk protein) encoded by the nucleic acid inserted in the vector is synthesized in the host cell in which the vector is transfected and can be readily purified.

The term "fusion protein" refers to two combined polypeptide segments that are not normally joined together and found in nature. Examples of such fusion proteins include a Dkk protein fused to an affinity label (e.g., a His5, His6 or c-myc tag). In some aspects, the fusion protein may also have a protease cleavage site introduced between the two heterologously fused proteins. Methods of inserting protease cleavage sites in fusion proteins are known in the art.

A nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

By "mammalian host cells" is meant a host cell derived from a mammal for expressing a Dkk protein. Most preferably, the host cell includes but is not limited to HEK293T cells, HEK293E cells, HEK293F cells, HEK293 EBNA cells, CHO cells, COS cells, HeLa cells, NIH3T3 cells, PER.C6 cells and PC12 cells.

"Biologically active", when used in conjunction with any of the recombinant Dkk proteins discussed herein, means a Dkk polypeptide that exhibits or shares an effector function of native Dkk. For example, a principal effector function of Dkk1 is its ability to bind LRP5, or to inhibit Wnt3a activity, and induction of secondary axes in *Xenopus* injection studies.

"Biological property" when used in conjunction with any of the recombinant or synthetic Dkk's described herein means having an effector or antigenic function or activity that is directly caused by or performed by the native Dkk protein. The effector or antigenic function or activity of the native Dkk protein can include denatured forms of the native Dkk protein. Effector functions include but are not limited to ligand binding (e.g., binding to LRP5 by Dkk1), and regulation of the Wnt activity (e.g., inhibition of Wnt3a signaling by Dkk1), differentiation and/or proliferation of cells (especially proliferation of cells).

| 1.2 Acronyms | |
|---|---|
| APMSF | (4-amidinophenyl)methane sulphonyl fluoride |
| AUC | analytical ultracentrifugation |
| BSA | bovine serum albumin |
| CD | circular dichroism |
| CHAPS | 3-[(3-cholamidopropyl)dimethylammonio]-1-propane-sulfonate |
| CHES | 2-(cyclohexylamino)ethanesulfonic acid |
| CM | culture media |
| Co-IP | co-immunoprecipitation |
| cpm | counts per minute |
| Dkk | Dickkopf |
| dn/dc | change in refractive index with concentration |
| DMSO | dimethyl sulfoxide |
| DTT | 1,4-dithiothreitol |
| ECD | extracellular domain of LRP5 or LRP6 |
| EDTA | ethylenediaminetetraacetate |
| EGTA | ethylene glycol-O,-O'-bis(2-amino-ethyl)-N,N,N',N'-tetraacetic acid |

-continued

| 1.2 Acronyms | |
|---|---|
| ESI-MS | electrospray ionization mass spectroscopy |
| FCS | fetal calf serum |
| GSK-3 | glycogen synthase kinase-3 |
| GuCl | guanidine chloride |
| hDkk1 | human Dkk1 |
| HEPES | 4-(2-hydroxy-ethyl)-1-piperazine ethanesulfonic acid |
| HRP | horseradish peroxidase |
| HTS | High-throughput screening |
| IPTG | isopropyl β-D-thiogalactoside |
| kD | kilodalton |
| LBD | ligand binding domain of LRP5 or LRP6 |
| LEF | lymphocyte enhancer factor |
| MES | 2-(N-morpholino)ethanesulfonic acid |
| MOPS | 3-(N-morpholino)propanesulfonic acid |
| NP-40 | polyethylene glycol-p-isooctylphenyl ether (Nonidet P40) |
| N-BOG | N-octyl-β-D-glucoside |
| PBS | phosphate buffered saline |
| PIPES | 1,4-piperazinediethanesulfonic acid |
| PMSF | phenylmethane sulphonyl fluoride |
| PVDF | polyvinylidene fluoride |
| RT | room temperature |
| SDS-PAGE | sodium dodecyl sulfate polyacrylamide gel electrophoresis |
| SEC-MALLS | size exclusion chromatography-multi-angle lazer light scattering |
| Sed-Vel. | Sedimentation velocity |
| Sed-Equil. | Sedimentation equilibrium |
| TAPS | N-tris(hydroxymethyl)methyl-3-amino-propanesulfonic acid |
| TBST | Tris buffered saline with 0.1% Tween-20 |
| TLCK | (N-tosyl-L-lysine chloromethyl ketone) |
| TPCK | (N-tosyl-L-phenylalanine chloromethyl ketone) |
| TR-FRET | time resolved fluorescence resonance energy transfer |
| T-X-100 | Triton-X-100 |
| Y2H | Yeast two-hybrid |

2. Methods of Synthesizing Dkk1

Although the methods and description are primarily directed to Dkk1, the methods are also contemplated for use in synthesizing and purifying other members of the Dkk family. Thus, the examples and description should be construed to encompass the other members of the Dkk family and not just Dkk1, which is exemplified in detail below.

2.1 Construction of Dkk1 Nucleic Acids and Expression of Dkk Protein

A method of preparing large quantities of biologically active Dkk1 protein is described as follows. A Dkk1 encoding nucleic acid is placed into a vector capable of replication in a mammalian host cell. Preferably, the Dkk1 is a mammalian sequence. More preferably, the nucleic acid encodes a full-length human Dkk1 protein (GenBank Accession No. AF177394). The vector can be any vector capable of replication and expression in the host cell of interest. For example, the vector can be pcDNA3.1/myc-His (Invitrogen, Calif.; Cat. No. V800-200). Other suitable vectors include, but are not limited to, any mammalian expression vectors available from such manufacturers as Invitrogen, Novagen, Qiagen, and BDBBiosciences-CLONTECH. The entire open reading frame of Dkk1 can be amplified and cloned into the BamH1/Xba1 sites of pcDNA3.1/myc-His so that the Dkk1 and C-terminal myc and His tags are in frame. The open reading frame (ORF) contains a signal sequence that allows for secretion of the Dkk protein into the extracellular space/media.

The vector containing the nucleic acid encoding Dkk1 is transfected into a mammalian host cell using, for example, Lipofectamine2000® (Cat. No. 11668; Invitrogen, Calif.). Other suitable transfection agents include but are not limited to Clonfectin (Clontech), Transfectam (Promega), Effectene (Qiagen), and Superfect (Qiagen). Other methods of transfecting mammalian cells are known in the art, including but not limited to calcium phosphate, DEAE dextran and electroporation. See, e.g., Ausubel et al. (CURRENT PROTOCOLS IN MOLECULAR BIOLOGY, Greene Publishing Co., NY, 1995); Sambrook et al. (MOLECULAR CLONING: A LABORATORY MANUAL, 2nd Ed. Cold Spring Harbor Laboratory Press, 1989); and SHORT PROTOCOLS IN MOLECULAR BIOLOGY: A COMPENDIUM OF METHODS FROM CURRENT PROTOCOLS IN MOLECULAR BIOLOGY (Frederick M. Ausubel et al., April 1999) for additional methods and details available in the art. The mammalian host cell preferably is HEK293T cells (ATCC No. CRL11268); HEK293T cells are a highly transfectable derivative of the HEK293 cell line into which the temperature sensitive gene for SV40 T-antigen was inserted. However, suitable mammalian host cells include those discussed supra. The majority of these cell lines is immortalized and can be used for long periods of time. Generally, however, cells are typically passaged for a maximum of 20 passages before new stocks are used. Cells transfected with the Dkk1 expressing nucleic acid are then cultured under conditions suitable to permit secretion of the Dkk1 protein into the culture media. Conditions for culturing the HEK293T cells are discussed in the examples below as well as generally herein. The conditions for culturing other cell lines such that they secrete Dkk1 or other Dkk protein into the culture media would be known in the art. See, e.g., R. IAN FRESHNEY, CULTURE OF ANIMAL CELLS—A MANUAL OF BASIC TECHNIQUE ($4^{th}$ ed., Wiley-Liss 2000).

Preferably, the Dkk1 when synthesized is tagged with an affinity label. The affinity label can be attached to either the carboxy or amino terminus of the polypeptide, and preferably on the carboxy terminus. Affinity labels include, but are not limited to, histidine (His) tags, glutathione-S-transferase, and maltose binding protein. Other tags include glutathione S-transferase (GST) tags, six-His tags, calmodulin binding peptide (CBP), FLAT tags, IBA GmbH's Strep-tag II™, pMAL™ system, and the like. For various tags and systems to use with these tags see, e.g., A. Constans, "Protein Purification II:Affinity Tags," 2002, *The Scientist* 16(4): 37. During purification, these tags will be recognized by an affinity ligand. Affinity ligands include but are not limited to antibodies, metal, maltose and glutathione, as discussed also below. Preferably, the Dkk protein is Dkk1 and is His tagged. The protein is purified using a metal affinity ligand (e.g., a nickel column). Other metal columns for use with a His tag include cobalt, zinc, copper and iron (Wong et al., 1991, *Separation and Purification Methods* 20: 49-106); see also A. Constans, "Protein Purification II: Affinity Tags," 2002, *The Scientist* 16(4): 37.

More specifically, HEK293T cells are grown in appropriate culture media, such as DMEM supplemented with 10% fetal calf serum. Cells should be plated at 90-95% confluency at the time of transfection. The liposfectamine2000® transfection protocol can be performed following the manufacturer's recommendations (Invitrogen, Calif.). As discussed, other transfection systems can alternatively be used. Briefly, Dkk1 DNA and lipofectamine are combined in an appropriate ratio to create Lipofectamine:DNA complexes. These complexes are then added to the cultured cells and are incubated at 37° C. for 5 hours post-transfection. After incubation, the media is replaced with serum-free media and incubated about another 48 hours. Secreted protein can be detected in the conditioned media after incubation from about 12 hours to about 72 hours. Peak levels of Dkk1 are detected at about 48 hours after transient transfection in HEK293T cells. After about 48 hours (e.g., 36-55 hours), the culture media is collected for protein purification.

3. Methods of Purifying Dkk1 from Culture Media

The culture media obtained above is clarified to remove cell debris by centrifuging the culture media for about 5-15 minutes at about 1,000-5,000 rpm and preferably at about 3,000 rpm for about 10 minutes. The culture media can then be frozen and stored at about −80° C. until later use, or can be further processed.

The clarified culture media (fresh or thawed) is then preferably adjusted to 0.5 M NaCl and 5 mM imidazole. Although NaCl is used, the skilled artisan will readily understand that other salts may be used, including but not limited to $CaCl_2$, LiCl and KCl. The concentration of salt in the media is adjusted to about 500 mM or less. The concentration of salt in the media is adjusted to about 500 mM to prevent non-specific hydrophilic/ionic interactions with the matrix and to inhibit protease activity in the mixture.

Imidazole can be adjusted from 0 to about 20 mM. Imidazole prevents non-specific proteins from binding to the purification column, such as those proteins with histidine sequences.

Ethanol aids in preventing non-specific binding by partially denaturing the protein. Ethanol in the range of about 2% to about 5% in the culture media aids in purification. Ethanol amounts added that are greater than 5% denature the protein and should be avoided.

PMSF is an inhibitor of serine and cysteine proteases. Given that any one protease inhibitor is active against a limited set of enzymes, generally a cocktail of protease inhibitors are used. Such cocktails can be purchased in the form of prepared tablets, e.g., Roche's complete EDTA-free protease inhibitor cocktail tablet (Cat. No. 1873580). Protease inhibitors include but are not limited to (4-amidinophenyl)methane sulphonyl fluoride (APMSF), amastatin, antipain, bestatin, benzamidine, chymostatin, 3,4-dichloroisocoumarin, DFP, phenylmethane sulphonyl fluoride (PMSF), E-64 (Boehringer Mannheim), elastatinal, leupeptin, pepstatin, 1,10-phenanthroline, phosphoramidon, heavy metals (e.g., $HgCl_2$, $AgNO_3$), iodoacetic acid, phosphoramidon, TLCK, and TPCK. Ranges of protease inhibitors to add would be pursuant to manufacturer's recommendations. As many inhibitors function on limited enzymes, combinations or cocktails of enzyme inhibitors are preferred. For example, the EDTA-free protease inhibitor cocktail tablet (Roche) can be used. Preferably the protease inhibitors or inhibitor cocktail used is EDTA (i.e. ethylenediaminetetraacetate) free. See, e.g. PROTEIN STRUCTURE—A PRACTICAL APPROACH (T. E. Creighton, ed., Oxford, England, 1989). The preferable protease inhibitor cocktail is free of EDTA or EGTA (ethylene glycol-O, —O'-bis(2-amino-ethyl)-N,N,N',N'-tetraacetic acid) since these molecules could damage the purification column.

The culture media can then be further clarified by filtering the media through a 0.45 micron filter to remove additional cellular debris and precipitates.

The clarified culture media can then be further purified using an affinity column, such as a nickel column as discussed in the examples below. The salts and compounds used are dependent on the tagged affinity label used. For His-tagged Dkk1, cobalt, zinc, copper and iron columns can also be used. Alternatively, beads can be mixed with the culture media and the protein isolated using, for example, magnetic beads. Columns can be obtained that are prebound with the metal of interest or pre-charged. The columns are prepared for gradient purification of the protein. Fractions containing the desired Dkk protein are then collected and pooled after testing the amount of protein in each fraction. Such testing can be performed by Western blot, dot blot, ELISA, or other procedures known in the art.

The pooled fractions can then be concentrated by any method known in the art. For example, Centricon concentration units can be utilized according to the manufacturer's instructions, as discussed in the examples provided below. Once the protein has been concentrated in the desired medium, the protein can be stored at −80° C. until needed. For example, the protein can be concentrated using YM30 Centricons produced by Millipore in a PBS buffer with about 0.1 to about 1 mM EDTA (or any 0.1 incremental value in between and preferably about 0.5 mM) and about 0.05% to about 0.15% Tween-20 (or any 0.05% incremental value in between and preferably about 0.1%). Alternative methods of concentrating Dkk1 include dialysis of the protein following $Ni^{2+}$ chromatography (to remove the imidazole and subsequent rebinding and step elution to a new $Ni^{2+}$ column). The protein can then be re-dialyzed or subjected to equilibrium dialysis to remove the imidazole. Other methods of further purifying the protein include but are not limited to vacuum dialysis, ammonium sulfate precipitation followed by dialysis, and affinity chromatography taking advantage of the c-myc or other appropriate affinity tag.

The presence of Tween-20 (or other comparable detergents) and EDTA is necessary for better yields. In the absence of Tween-20 and EDTA, the yield of Dkk1 is low (less than about 1 mg of protein per liter of media). When Tween-20 or EDTA are used separately, a minor (i.e., about 1.2 to about 1.5 fold) increase in yield is observed. However, when EDTA and Tween-20 are combined, these reagents work synergistically to increase the overall yield 5-fold as compared to their absence, whereby about 5 mg or more of Dkk1 is obtained per liter of media following over-expression and purification.

In addition, Dkk1 expressed in HEK293 EBNA cells has been purified by $Ni^{2+}$ chromatography and concentrated (as described previously) in the presence of 0.7% N-octyl-β-D-glucoside with yields exceeding 5 mg/ml. The concentrated Dkk1 was then subjected to Superdex-200™ column chromatography using PBS containing 0.5 mM EDTA and 0.7% N-octyl-β-D-glucoside. The resulting yield exceeded 80% and increased the purity greater than 1.5-fold. Dkk1 is also stable in Superose-12™ and Superdex-200™ column chromatography systems, where the mobile phase is PBS containing about 0.5 mM EDTA and about 0.005% Tween-20, or about 0.05% to about 0.7% N-octyl-β-D-glucoside.

Dkk1 is also stable to preparative gel filtration chromatography following $Ni^{2+}$ affinity chromatography and subsequent concentration. The yield is >80% at a preparative scale (about 50 mg quantities) and >50% at semi-preparative scale (about 0.5 to about 2 mg), where the mobile phase is PBS containing 0.5 mM EDTA and Tween-20 (about 0.005 to about 0.1%) or N-BOG (about 0.05 to about 0.7%). Dkk1 is also stable to dialysis at preparative (>10 mg) and semi-preparative scales (1-10 mg) quantities. Here >95% yields are obtained when dialyzed in PBS containing 0.5 mM EDTA and 0.1% Tween-20 or 0.7% N-BOG.

The presence of Tween-20 (or other comparable detergents) and EDTA is necessary for better yields. The addition of about 0.1% Tween in the concentration steps helps prevent non-specific binding to the membrane. Other detergents that can be used include but are not limited to CHAPS, octylglucoside, triton X, and NP-40, as long as the detergent does not inhibit the activity of the protein.

Preferably, once the Dkk protein is isolated and purified, its concentration is quantified and qualified. For example, the protein can be run on a sodium dodecyl sulfate (SDS) polyacrylamide gel by electrophoresis and compared to a protein standard for concentration and purity. The amount of protein present can be assessed by Coomassie blue or silver-staining procedures, as would be known in the art. See, e.g., SAMBROOK ET AL., MOLECULAR CLONING: A LABORATORY MANUAL (Cold Spring Harbor Press 1989). Standardized control samples to assess quantity can include other Dkk1 proteins produced by other sources, as well as other known constant proteins, such as bovine serum albumin (BSA).

4. Methods of Storing Dkk1

The Dkk1 obtained either after synthesis or purification optimally can be stored in the solution it was concentrated in. For example, if Centricons were used to concentrate Dkk, then the buffer preferably is PBS with about 0.5 mM EDTA and about 0.1% Tween-20. Dkk1 can also be stored in PBS containing about 0.5 mM EDTA and about 0.005% to about 1% Tween-20, or it can be stored in PBS containing about 0.5 mM EDTA and about 0.05 to about 0.7% N-octyl-β-D-glucoside. Alternatively, the Dkk can be placed into PBS with about 0.5 mM EDTA only. Both solutions can then be frozen in liquid nitrogen and stored long term at about −80° C. Preferably, the Dkk1 is stored at about −80° C. in the same buffer in which it was concentrated. The protein is stable for several months if stored at about −80° C.; multiple freeze-thawings are avoided.

5. Characterization of Dkk1

The protein can be characterized by numerous methods. Its molecular weight, quaternary structure and purity can be determined using SDS-PAGE or sedimentation methods. The solubility can be determined with static light scattering measurements. Protein conformation as well as secondary or tertiary structure can be obtained using fluorescence and/or circular dichroism spectroscopy. Protein thermal stability can be measured using differential scanning microcalorimetry. The features of the Dkk proteins obtained from the culture media of mammalian host cells transfected with a vector that expresses the Dkk protein can include any of the following general characteristics.

The molecular weight of a single polypeptide chain of a denatured protein can be measured via SDS-PAGE under reducing conditions. For example, the molecular weight of Dkk1 obtained from HEK293T cells is 40 kD±2.0 kD depending on the electrophoresis conditions used. This is different than the expected molecular weight of Dkk1 including the linkers and myc and His affinity tags, used for the exemplified production of Dkk1; the calculated molecular weight of Dkk1 with a myc and a His tag would be 32 kD. ESI-MS analysis provides molecular masses of about 36.1 to about 36.9 kD for the human Dkk1 protein.

The higher molecular weight obtained is likely due to the glycosyl moieties on the Dkk1 protein. The molar mass of the protein in solution can be obtained using a multi-angle laser light scattering method or analytical ultracentrifugation; both methods yield molar mass of protein in its native folded state. Moreover, such methods also provide insight into the shape and conformation of the protein in solution and in complex with its cognate receptor target. The thermal denaturation profile of the protein using spectroscopic or differential scanning calorimetric methods is another important tool to determine the homogeneity and stability of the protein which is unique to the sequence and the conformation of the protein.

It is expected that different mammalian host cells would also produce a Dkk1 protein with approximately the same molecular weight as the Dkk1 protein obtained from HEK293T cells. The determination of molecular weight can also confirm the presence (as opposed to the absence) of glycosyl moieties on the protein. The presence of glycosyl groups similar to those found on native Dkk is important for the protein to interact with its native ligands and exhibit its native activity. For example, Dkk1 produced from insect cells and insoluble inclusion bodies from bacteria were significantly less active to inactive in various assays as the Dkk1 produced in HEK293T cells.

An example of a characteristic that the Dkk1 protein should have is its ability to inhibit Wnt3a mediated signaling. This Dkk inhibitory activity can be measured by using, for example, the TCF-luciferase assay described in the examples. A negative control that can be used is Dkk1C220A, which is a Dkk1 mutant that is known to lack Dkk1 activity. Preferably, the purified Dkk1 should inhibit Wnt3A mediated signaling. Additional detail is provided in the examples below. For example, 40 ng of Dkk1 should inhibit Wnt3A activity as measured by a TCF/Renilla assay by about at least 50% or more, more preferably by at least 60%, and most preferably by at least 75% as compared to the Dkk1 mutant C220A V5His, which is an inactive form of Dkk due to a cysteine to alanine mutation at residue 220 of the Dkk1 polypeptide. Alternatively, the purified Dkk should have an activity of at least about 75% inhibition at 50 ng/well of Dkk and at least about 80% inhibition at about 100 ng/well of Dkk (FIG. 4) with an IC50 of approximately 1.25 pM.

The Dkk1 protein can also be measured for its ability to co-immunoprecipitate LRP5 and LRP6, receptors for Dkk1. For example, Dkk1 can be tagged with a marker, such as myc. The tagged Dkk1 can then be identified using an anti-myc antibody. Other such markers are known in the art as discussed herein. If the Dkk1 protein co-immunoprecipitates with another protein, the antibody can be used to detect the complex. Greater detail for such co-immunoprecipitation experiments is provided below in the Examples.

The ability of Dkk1 protein to form a complex with LRP5 and LRP6 can be characterized using spectroscopic methods such as circular dichroism (CD) or fluorescence and also using transport-based methods, such as AUC and SEC-MALLS, where the individual proteins are identified by distinct unfolding temperatures and molar mass and the formation of the complex increases the molar mass and the stability of the protein.

The Dkk proteins can be further characterized by their heat stability, pH stability, reactivity to known Dkk protein antibodies, isoelectric point, solubility in various solvents, co-immunoprecipitation assays, *Xenopus* assays, tunicamycin related activity assays, protein conformation, as well as secondary, tertiary and quaternary structure as would be known in the art.

EXAMPLES

Although the present invention has been described in detail with reference to examples above, it is understood that vari-

Example 1

Synthesis of Dkk1

HEK293T cells (ATCC Cat. No. CRL11268) were plated at 90-95% confluency in DMEM media supplemented with 10% fetal calf serum. Specifically, cells were trypsinized and plated the day before transfections at $9.6 \times 10^6$ cells per T75 flask. Human Dkk1 (GenBank Accession No. AF177394) was cloned into the pcDNA3.1/myc-His vector (Invitrogen) containing c-myc and His6 tags at the carboxy terminus as follows. A clone containing the full length Dkk1 open reading frame in the pC52 vector was subjected to PCR using PFU Turbo Polymerase (Stratagene, Cat. No. 600250). 5'-TTTTTTGGATCCGCCACCATGATGGCTCT GGGCG-CAG-3' was used as forward primer and 5'-TTTTTTTCTA-GAGTGTCTC TGACAAGTGTG-3' was used as reverse primer. The 0.8 kb PCR product was purified from an agarose gel using the Qiaex II gel extraction kit (Qiagen Cat. No. 20021) as specified by the manufacturer. The purified PCR product was digested with BamHI and XbaI and ligated to pcDNA3.1/myc-His (Invitrogen Cat. No. V800-20) which was linearized with the same enzymes. The ligation mix was transformed into ElectroMAX DH10B cells (Invitrogen Cat. No. 18290-015) according to the manufacturer's instructions; clones containing the plasmid were isolated and amplified in LB Broth containing 100 µg/ml ampicillin. The clones were sequenced to confirm the correct sequence and that the Dkk1 and myc-His sequences were in the same open reading frame.

HEK293T cells were transfected with the pcDNA3.1 vector containing the nucleic acid expressing Dkk1 as follows. Twelve µg of pDNA3.1-Dkk1mychis DNA was diluted into 900 µL of OPTI-MEM media (Invitrogen). Then, for each T75 flask, 45 µL LIPOFECTAME 2000® (Invitrogen, Cat. No. 11668) was diluted into 900 µL of OPTI-MEM and then incubated for about 5 minutes at room temperature. Once the diluted LIPOFECTAMINE 2000® is prepared, it must be combined with the diluted DNA within 30 minutes of its preparation. However, this LIPOFECTAMINE 2000® procedure can be done in bulk for multiple flasks. After combining the diluted DNA with the diluted LIPOFECTAMINE 2000®, the mixture was incubated at room temperature for about 20 minutes to allow DNA-LIPOFECTAMINE 2000®complexes to form.

The formed DNA-LIPOFECTAMINE 2000® complexes (1.8 mL) were added directly to the T75 cell-containing flask and the cells treated pursuant to manufacturer's instructions. It should be noted that the cell media contains serum but is free of antibiotics.

Cells were then transfected at 37° C. for about 4 to 6 hours. After culturing, the media was removed and the cells were washed briefly with OPTI-MEM to remove the residual serum. 12 mLs of fresh OPTI-MEM was then added to each T75 flask. Cells were cultured for 48 hours and the 12 mLs of OPTI-MEM conditioned media was collected. The conditioned culture media was centrifuged for 10 minutes at about 3,000 rpm to remove cell debris. The culture media was then aliquoted and frozen at −80° C.

As would be evident to the artisan of ordinary skill, this procedure can be scaled up depending on the need. For example, the same procedures can be used wherein ten T150 flasks are used instead of T75 flasks. For this procedure, clearly, the amounts used would merely be doubled.

Example 2

Purification of Dkk1

The Dkk1 protein was purified from the culture media (see Example 1) as follows. Nickel columns were prepared using a 5 mL HiTrap chelating column (5 mL; Amersham Pharmacia Biotech, Cat. No. 17-0-109-01) following the manufacturer's instructions. The column was washed first with 40 mL of deionized water. The nickel was loaded by passing 40 mL of 50 mM $NiSO_4$ through the column followed by washing again with 40 mL deionized water.

| Buffer A | Buffer B |
|---|---|
| 50 mM $KPO_4$, pH 8.0 | 50 mM $KPO_4$, pH 8.0 |
| 500 mM NaCl | 500 mM NaCl |
| 10% Glycerol | 10% Glycerol |
| 5% Ethanol | 5% Ethanol |
| 20 mM Imidazole | 1000 mM Imidazole |

For Buffers A and B, a 1 M KPO4 (pH 8) stock buffer was prepared by mixing 96-mL of 1 M $K_2HPO_4$ with about 6 mL 1 M $KH_2PO_4$.

Approximately 300 mL of conditioned media was thawed and adjusted to 500 mM NaCl, 5 mM imidazole (pH 7.0) and 1 mM phenylmethylsulfonyl fluoride PMSF). A protease inhibitor cocktail was added in an amount of 1 mL per 100 mL of adjusted conditioned media. The protease inhibitor cocktail was prepared by dissolving one complete, EDTA-free protease inhibitor cocktail tablet (Roche, Cat. No. 1873580) in 2.5 mL water, according to the manufacturer's instructions. This was performed just prior to use, as the activity lasts for approximately 8 hours at 4° C. The inhibitor cocktail prepared as described above was also added to both Buffer A and Buffer B in an amount of 1 mL per 100 mL. The protease-treated media was then filtered through a 0.45 µM filter prior to loading the media on the nickel column (i.e., $NiSO_4$; HiTRAP chelating column from Amersham/Pharmacia; Cat. No. 17-0-109-01).

The nickel column was pre-equilibrated with 30 mL of the protease treated Buffer A. The protease treated, filtered culture media was then loaded on the nickel column. This step was followed by a wash step using 20 mL Buffer A.

The protein was eluted using a gradient of 80 mL. The 80 mL comprised 100% BufferA::0% Buffer B to 60% Buffer A::40% Buffer B. This was then followed by a 40 mL-gradient consisting of 60% Buffer A::40% Buffer B to 0% Buffer A::100% Buffer B.

Collected fractions were checked by a dot blot procedure, although other methods can be used as well. The dot blot analysis was performed as follows. Twenty-five µL of the eluted fractions were added to 100 µL PBS in a 96-well assay plate. The dot blot apparatus (Schleicher & Schuell Minifold®I) was prepared using 4×5.25 inch cut PVDF membrane backed by two sheets of PBS-soaked blotting paper as described by the manufacturer (Schleicher & Schuell). The polyvinylidene difluoride (PVDF) membrane was activated by a 2 min. wash in 100% methanol followed by a 2 minute wash in transfer buffer (25 mM Tris, 192 mM glycine, 20% methanol at pH 8.3). Samples were dotted onto the membrane in 125 µL amounts. Then the vacuum was turned on such that the samples were filtered through the membrane. Once the samples were filtered through the membrane, the membrane was blocked using TBST (20 mM Tris- HCl, pH 7.6; 137 mM NaCl; 0.1% Tween-20) containing 5% non-fat dried milk and 1% bovine serum albumin (BSA) at 4° C. The blocking step can be performed from about 1 hour to overnight.

Immunodetection was performed using a 1:5,000 dilution of horseradish peroxidase (HP) anti-myc antibody (Invitrogen, Cat. No. R951-25) in TBST containing 5% non-fat dried milk and 1% BSA. The PVDF membrane was incubated in the presence of the antibody for about 1 hour at room temperature with agitation. The membrane was then washed three times in TBST for 5 minutes for each wash. Protein was visualized using the ECL Plus Western Blot Detection System (Amersham Cat. No. RPN2132) and then exposed to X-ray film.

Peak Dkk1 containing fractions were pooled. EDTA and Tween-20 were added to a final concentration of 0.5 mM and 0.1% respectively.

Four Centricons (YM30; Millipore, Cat. No. 4209) were pre-washed with PBS supplemented with 0.5 mM EDTA and 0.1% Tween-20. Pooled Dkk1 fractions were loaded into the washed Centricons and concentrated by centrifuging at 3,000 rpm at 4° C. for 30 minutes to concentrate the fractions to 200 µL. Longer spins were necessary for some of the fractions. The Centricons were filled with more Dkk1 containing fractions, and the step was repeated until all the fractions were concentrated. Dkk1 is stable in PBS containing Tween and N-octyl-β-D-glucoside concentrations ranging from 0.005 to 0.1% and 0.05 to 0.7%, respectively, and 0.5 mM EDTA.

To change the buffer on the concentrated fractions to PBS supplemented with 0.5 mM EDTA and 0.1% Tween-20, the concentrated fraction were adjusted to 2 mL with PBS containing 0.5 mM EDTA and 0.1% Tween-20. The samples were then re-concentrated as discussed above. This process was performed three times. The sample was then hand pipetted up-and-down several times while avoiding the membrane. The Centricon was then inverted such that the sample flowed into the collection tube and the unit was centrifuged at 1,000 rpm for 2 minutes to collect the concentrated sample. At this point the volume should be ≦1 mL.

Here, the inclusion of EDTA and Tween-20 is necessary for good yields of Dkk1. Using PBS alone in the absence of these agents resulted in an 80% or 4-fold reduction in yield. Other detergents, such as Tween-20 and N-BOG have been used successfully.

Alternatively, Dkk1 can be concentrated to 2 to 3 mg/ml using Centricons pre-washed in PBS supplemented with 0.5 mM EDTA and 0.1% Tween-20. To remove the imidazole, Dkk1 can be subjected to dialysis into PBS containing 0.5 nM EDTA and 0.1% Tween 20 or 0.7% N-BOG. This dialysis step results in <5% loss of protein. Likewise, Dkk1 protein from the affinity purification step can be collected in buffer containing low concentrations of N-BOG (about 0.05%) or exchanged with another detergent by equilibrium dialysis We have also been able to further purify Dkk1 by preparative size exclusion chromatography. Dkk1 expressed in HEK293 EBNA cells was purified by $Ni^{2+}$ chromatography and concentrated in excess of 5 mg/ml in the presence of 0.7% N-octyl-β-D-glucoside or 0.1% Tween-20. The concentrated Dkk1 was then subjected to Superdex®™ column chromatography using PBS containing 0.5 mM EDTA and 0.7% N-BOG or 0.1% Tween-20. The resulting yield exceeded 80% and increased the purity 1.2-fold. The resulting protein was then re-concentrated to 3.5 mg/ml with an overall yield of 4.8 mg of Dkk1/L of media.

Dkk1 is also stable to Superose-12™ column chromatography where the mobile phase is PBS containing 0.5 mM EDTA and 0.005% Tween-20 or 0.05% N-octyl-β-D-glucoside.

Protein concentration was assessed using the Bradford assay; reagents were purchased from BioRad and used according to the manufactures instructions.

Protein purity was assessed by SDS-PAGE. Proteins electrophoresed on a SDS-PAGE gel were stained with Biosafe Coomassie stain (Bio-Rad, Cat. No. 161-0786).

Using this method, yields of Dkk1 averaged about 5 mg of protein per liter of conditioned media. Protein was then aliquoted and frozen with liquid nitrogen. Aliquoted samples were then stored 80° C.

In contrast, the amounts and quality of Dkk1 obtained from a *Drosophila* expression system and from bacterial inclusion bodies was not as robust. First, expression from the *Drosophila* expression system was performed by cloning the Dkk1 nucleic acid into the *Drosophila* expression vector, pMTBip (Invitrogen, Cat. No. K5130-01). The *Drosophila* S2 cell line was transfected using CellFECTIN reagent (Invitrogen, Cat. No. 10362-010) with pMTBip Dkk1 plus pCoBlast. Stable transfectants were selected using 25 µg/mL Blasticidin (Invitrogen, Cat. No. R210-01). The stable transfectants were induced with 0.5 mM $CuSO_4$ and conditioned media containing the Dkk1 was isolated 72 hours after induction. The yield of Dkk1 protein obtained from the conditioned media was estimated to be about 0.1 µg/mL, ~50 fold lower than described above, by Western blot.

The Dkk1 was also isolated from bacterial inclusion bodies using a bacterial expression system. For this approach, the Dkk1 nucleic acid was cloned into the bacterial expression vector pET23A (Novagen) and the vector then transformed into bacterial strain BL21 (Novagen). Bacteria were induced with IPTG (isopropyl β-D-thiogalactoside) and cell lysates were isolated. Dkk1 was primarily expressed in insoluble inclusion bodies which were isolated by standard protocols. Specifically, inclusion bodies were solubilized in either 8 M urea or 6 M guanidinium HCl and renatured by stepwise dialysis against decreasing amounts of urea or guanidine chloride in buffer containing 100 mM Tris-HCl, pH 8.0, 2 mM EDTA, 0.4 M L-arginine-HCl, 5 mM oxidized glutathione, 0.5 mM reduced glutathione, and 0.1 mM PMSF. Final dialysis was performed against 100 mM Tris-HCl, pH 8.0, 0.2 mM EDTA and 0.1 mM PMSF. The yield of Dkk1 protein using this procedure was approximately 10 µg/mL. However, as shown in the examples herein, the Dkk1 protein was not active to the same degree as that obtained from HEK293T cells.

Example 3

Comparison of Dkk1

Figure 2:
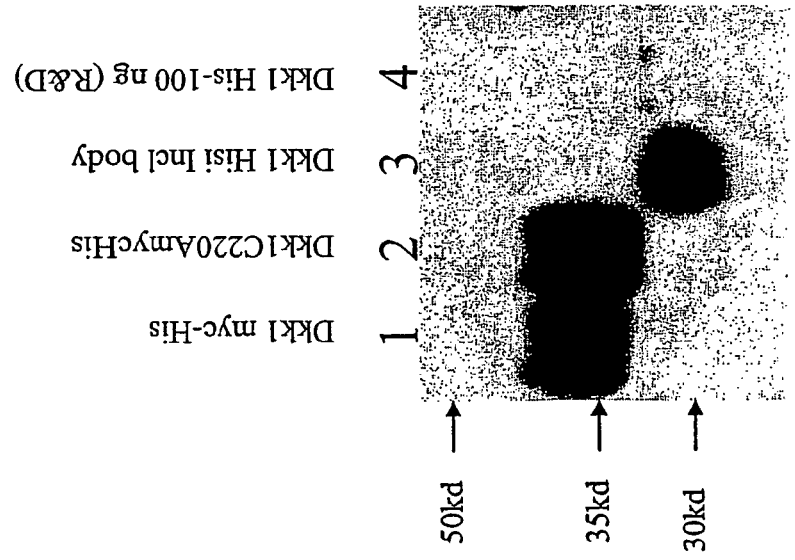
FIG. 2 Glycosylation of various forms of the Dkk1 protein. Dkk1 protein was electrophoresed on a 12% resolving, 4% stacking acrylainide ready gel (Bio-Rad, Cat. No. 161-1156) with Rainbow marker (Amersham, Cat. No. RPN 800). The gel was blotted to a PVDF membrane (Bio-Rad Cat. No. 162-0176) and immunodetected with 1:2,000 horseradish peroxidase (HRP)-labeled anti-6× polyHistidine monoclonal antibody (R&D Systems, Cat. No. MABO50H). Lane 1 is Dkk1 tagged with mycHis and produced by HEK-293T cells (25 μL of conditioned media from HEK293T cells transiently transfected with pcDNA3.1/myc-HisDkk1wt). Lane 2 is 25 μL of conditioned media from HEK293T cells transiently transfected with pcDNA3.1/myc-His mutant form of Dkk1, wherein the cysteine at position 220 has been changed to an alanine (Dkk1C220AmycHis). Lane 3 is 25 μL of Dkk1 renatured from bacterial inclusion bodies solubilized in 8 M urea. Lane 4 is 1 μL of 100 ng/L Dkk1 from R&D Systems (Cat. No. 1096DK/CF) purified from a baculovirus expression system. The presence of smaller proteins in lanes 3 and 4 demonstrates that the protein from the bacterial and baculovirus expression systems has a reduced amount of glycosyl moieties.

When the forms of bacterial, baculovirus-derived and HEK293T-cell derived Dkk1 were assessed on SDS-PAGE (FIG. 2), there was a notable difference in molecular weight between the forms due to the presence or lack of glycosyl moieties. As depicted in FIG. 2, the bacterial-derived Dkk1 (lane 3) had a significantly lower molecular weight than the HEK293T-cell derived Dkk1 protein. The baculovirus-derived Dkk1 (lane 4; commercially available from R&D Systems) also had a significantly lower molecular weight due to the protein having a different glycosylation pattern than that formed in mammalian cells (i.e., 33 kD±2 kD for R&D Systems Dkk1 versus 35 kD±2 kD for both the Dkk1 myc-His and Dkk1C220AmycHis).

Dkk1 protein was run on a 12% resolving, 4% stacking acrylamide-ready gel (Bio-Rad, Cat. No. 161-1156) with rainbow marker (Amersham, Cat. No. RPN 800). The gel was blotted to a PVDF membrane (Bio-Rad, Cat. No. 162-0176) and immunodetected with 1:2000 horseradish peroxidase (HRP) anti-6xHis monoclonal antibody (R&D Systems, Cat. No. MABO50H). Lane 1 has 25 µL of conditioned media from HEK293T cells transiently transfected with pcDNA3.1mychisDkk1 (wild-type). Lane 2 had 25 µL of conditioned media from HEK293T cells transiently transfected with pcDNA3.1mycHisC220A mutant. This mutant has a cysteine to alanine change at position 220 in the Dkk1 polypeptide. This mutation does not impact protein size, but does prevent the binding of Dkk1 to LRP5 protein, which is therefore a negative control for inhibition of Wnt activity. Lane 3 has 25 µL of Dkk1 renatured from bacterial inclusion bodies that had been solubilized in 8 M urea, as described in Example 2. Lane 4 has 1 µL of 100 ng/µL Dkk1 from R&D Systems (Cat. No. 1096DK/CF) purified from a baculovirus expression system. The band shift between lanes 3 and 4 as compared to that from lanes 1 and 2 demonstrates that the Dkk1 from bacterial and even baculovirus expression systems had a reduced amount of glycosyl groups.

The importance of glycosylation to the activity of the Dkk1 protein was tested as follows. Mammalian Dkk (highly glycosylated) produced according to Examples 1-2, tunicamycin treated mammalian Dkk1, bacterial Dkk1 (not glycosylated) and baculovirus Dkk1 (low glycosylation) were tested for activity. The activity for the various forms is summarized in the Table below and as described further in the examples. The Dkk1 produced by the method of Examples 1-2 had significantly better activity than any of the other Dkk1 forms, including the tunicamycin treated Dkk1.

When HEK293A cells were treated with tunicamycin, the cells secreted a non-glycosylated form of Dkk1. In brief, HEK293A cells were plated in 60 mm dishes and transfected with Dkk1 cDNA using the lipofectamine procedure described above. After 4 hours, the transfection mix was removed and the cells were washed with 1x OptiM. Fresh OptiM was added along with 0.2 µg/ml tunicamycin (Sigma; Cat. No. T-7765). Vector control samples were also treated with the same amount of tunicamycin. Conditioned media aliquots were collected at 24 hr, 48 hr and 72 hr and stored frozen after removing cell debris by centrifugation of the media for 10 minutes at 3,000 rpm. Dkk1 was assessed by PAGE and Western blotting using Dkk1 specific antibodies. 20 µL of the conditioned medium (with or without tunicamycin treatment) was electrophoresed on pre-case, 4% stacking and 12% resolving acrylamide gels (Bio-Rad). Once the gel was blotted to a PVDF membrane (Bio-Rad), it was treated with Dkk1 specific antibodies at an 1:250 dilution (10 µg/mL). The antibody reacting bands were visualized by the standard chemiluminescent method. The results obtained confirmed that tunicamycin treated cells produced a Dkk1 of a lower molecular weight than untreated cells. Tunicamycin is a known inhibitor of N-linked glycosylation.

Example 4

Deletion Mutants

Figure 10:
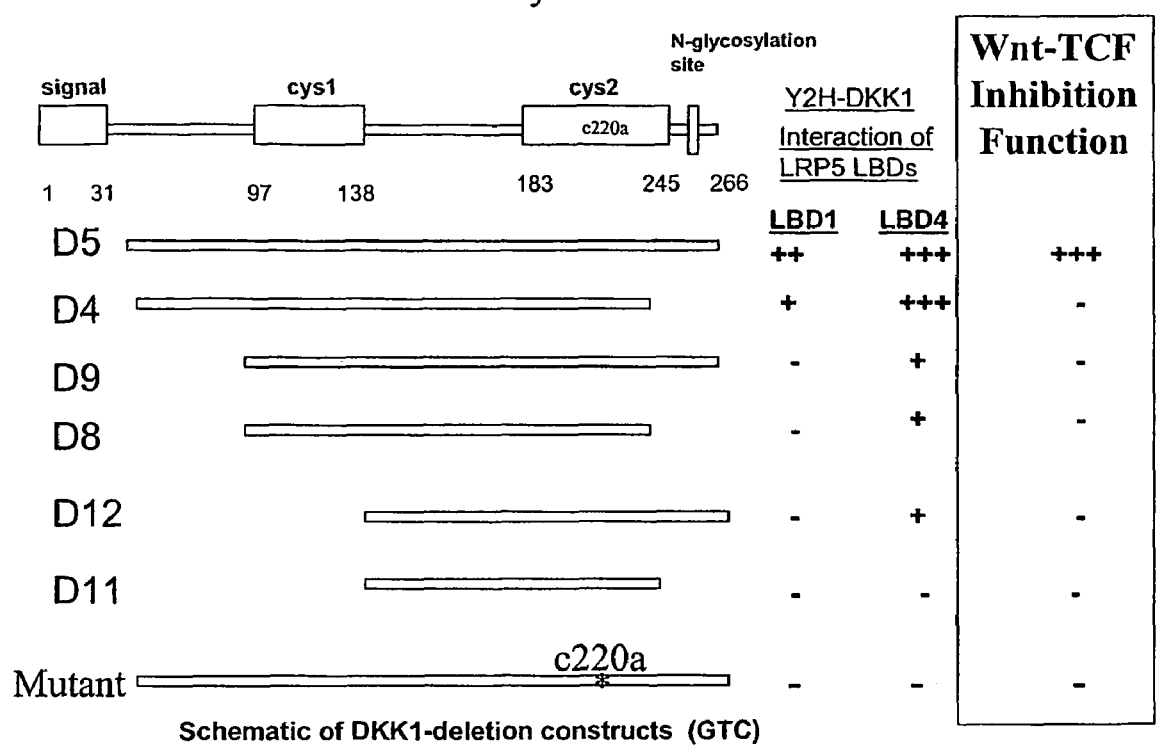
FIG. 10 Schematic Diagram of Dkk1 mutations in Dkk1 polypeptide and impact when testing for activity in binding the LRP4 LBD1 and LBD4 domains in a yeast two hybrid (Y2H) assay as well as Wnt-TCF activity as tested using a TCF-luciferase assay. The mutants are comprised of the following polypeptide sequences of Dkk1: D5 has amino acids 31-266; D4 has amino acids 31-245; D9 has amino acids 97-266; D8 has amino acids 97-245; D12 has amino acids 138-266; D11 has amino acids 138-245; C220A has amino acids 31-266, like the wild-type polypeptide except there has been a change at position 220 of a cysteine to an alanine.
Figure 11:
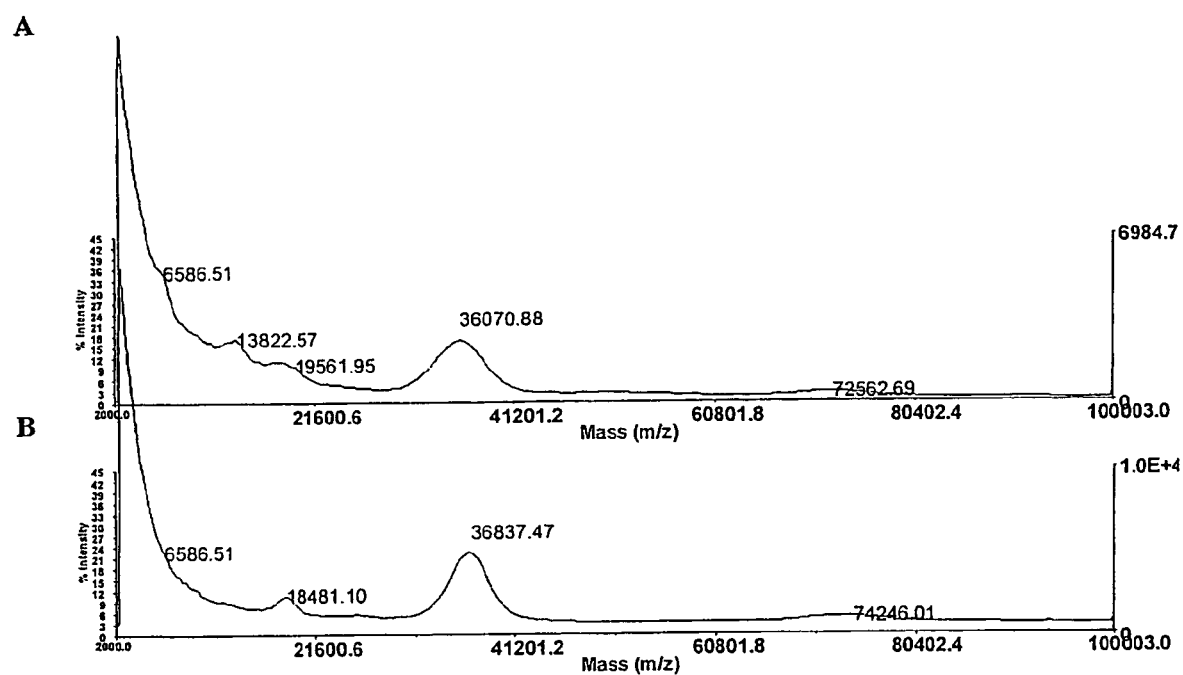
FIG. 11. ESI-MS analysis of over-expressed and purified Dkk1 from two unique sources. (A) Dkk1 expressed in HEK293 EBNA cells. Protein was purified as described in the document using $Ni^{2+}$ chromatography followed by Superdex-200 size exclusion chromatography. (B) Dkk1 expressed in HEK293T cells and purified following $Ni^{2+}$ affinity chromatography as described within the document.
Figure 12:
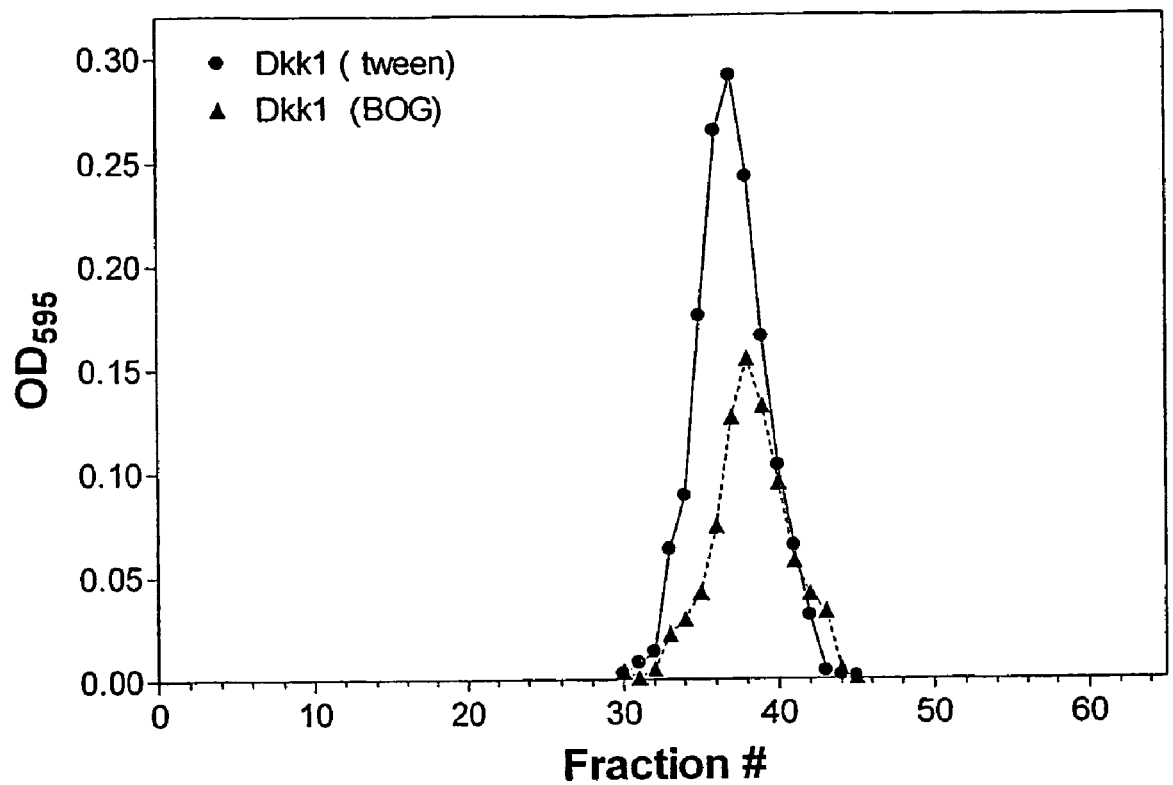
FIG. 12. Elution profiles of Dkk1 in PBS containing 0.05% N-BOG and 0.005% Tween-20. (▲) 0.5 mg or (●) 1 mg of Dkk1 purified in the presence of 0.7% N-BOG 0.1% Tween were subjected to preparative size exclusion chromatography (Superose-12, 10×300 mm column). Fractions (0.4 mL) were collected.
Figure 13A:
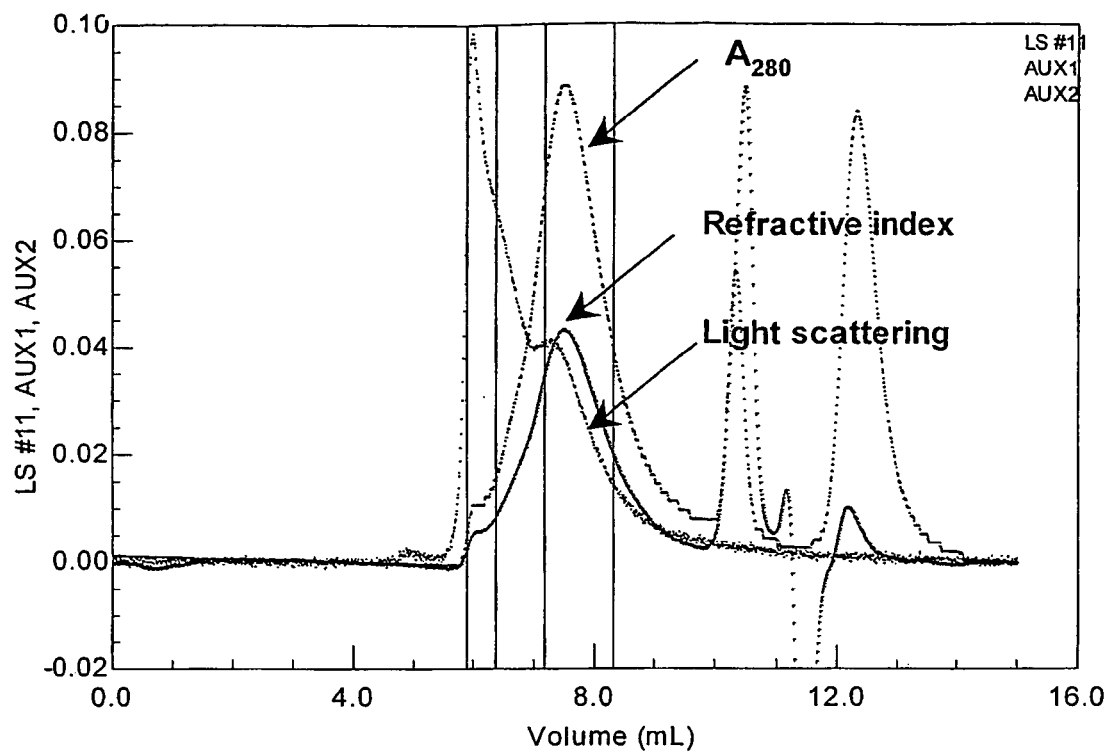
FIG. 13. SEC-MALLS Analysis of Dkk1. Dkk1 purified in the presence of 0.7% N-BOG (panel A) 0.1% Tween (panel B) was injected into a Bio-Sep 2000 (Phenomenex) column using PBS as the mobile phase and a flow rate of 0.5 ml/min. Protein was detected using a Wyatt optilab DSP refractometer, a Wyatt Dawn EOS, and an Agilent 1100 series photodiode array. Panels C and D represent the molar mass vs. volume and cumulative molar mass profiles, respectively, as determined from the Astra 4.90.07 software.
Figure 13B:
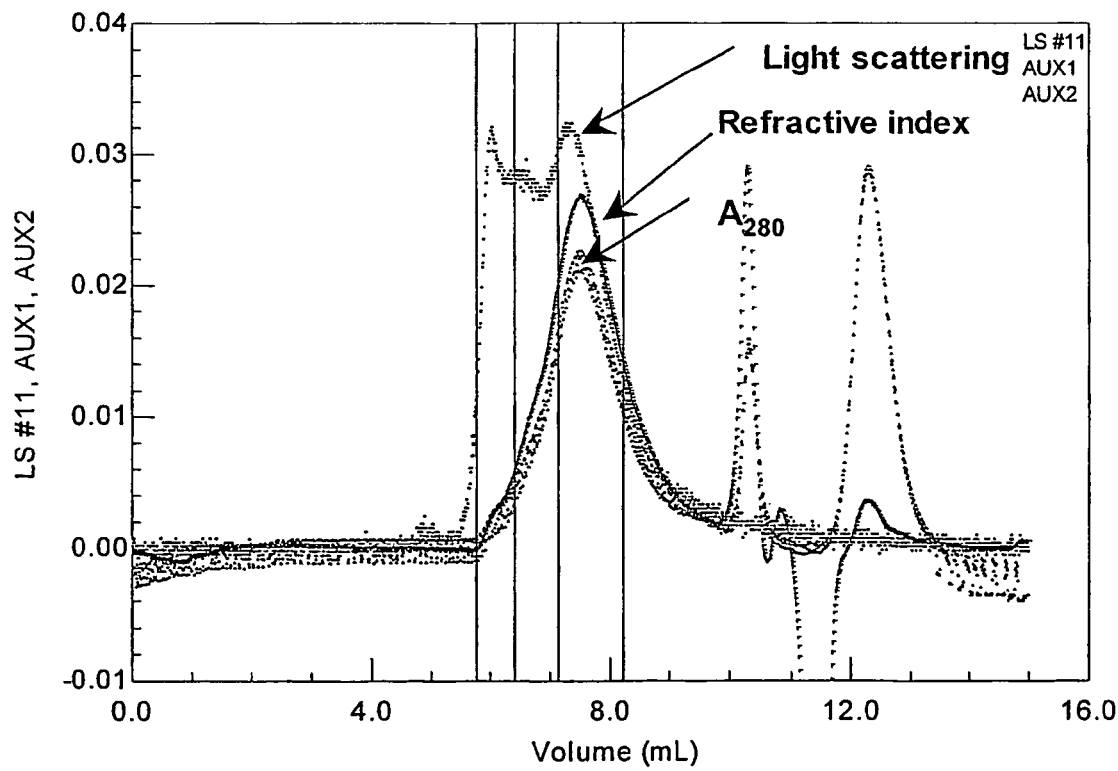
Figure 13C:
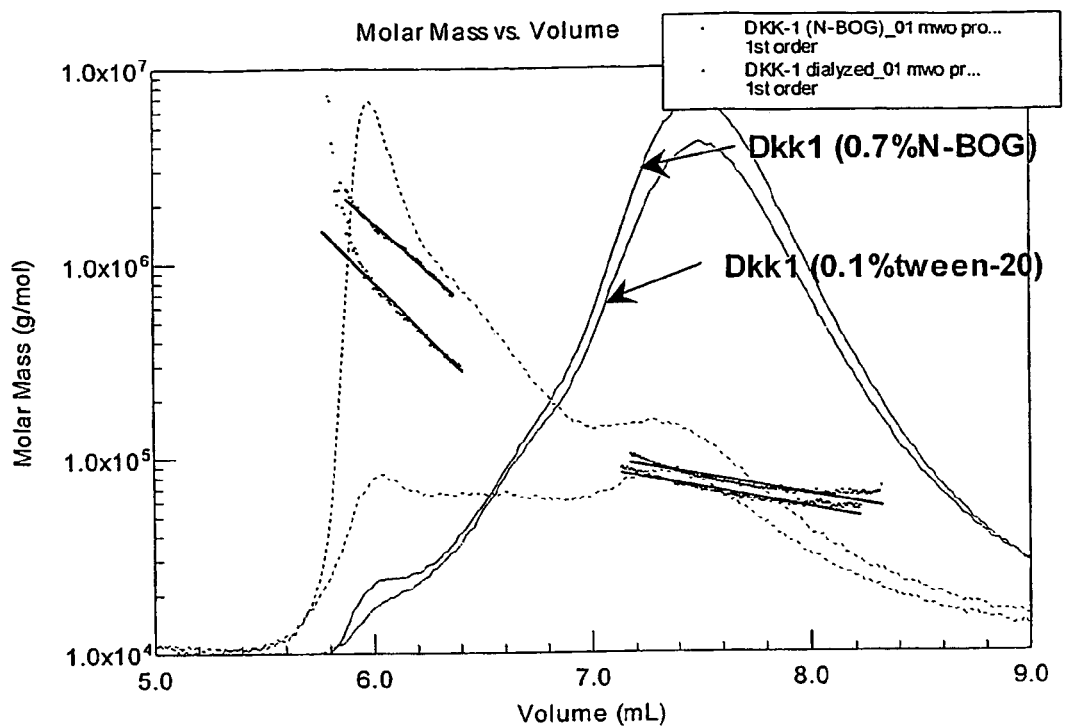
Figure 13D:
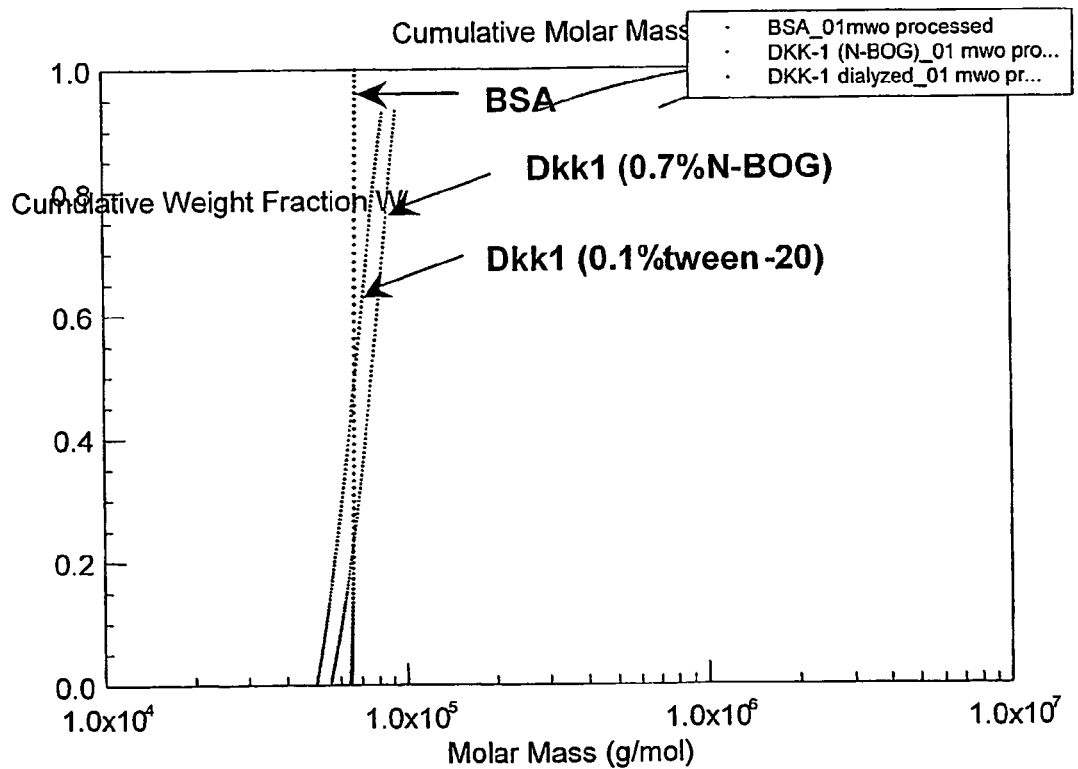
Figure 14B:
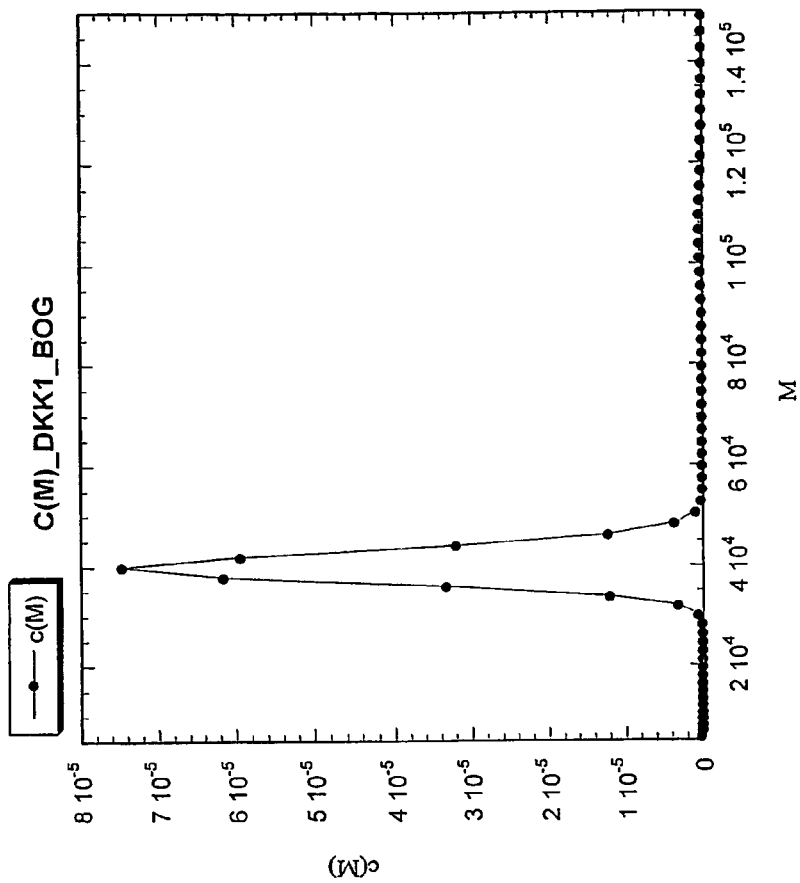
FIG. 14. Analytical ultracentrifugation analysis of Dkk1. Dkk1 was subjected to sedimentation velocity analysis of BEK293 EBNA derived Dkk1 centrifuged at 35,000 RPM at 20° C. Top, (panels A-B) middle and lower panels correspond to Sed-Vel analyses of the Dkk1 protein in PBS buffer containing 0.001% Tween, PBS alone and PBS containing 0.03% BOG. Sedimentation equilibrium analysis of Dkk1 (panels C and D) was performed using a Beckman XL-I analytical ultracentrifuge using 6-sector cells. Panels C and D represent the sedimentation profiles of Dkk1 centrifuged at 35 krpm. Panel C and D contains 1.66 uM Dkk1 containing 0.002% Tween-20 and 0.012% N-BOG, respectively.
Figure 14A:
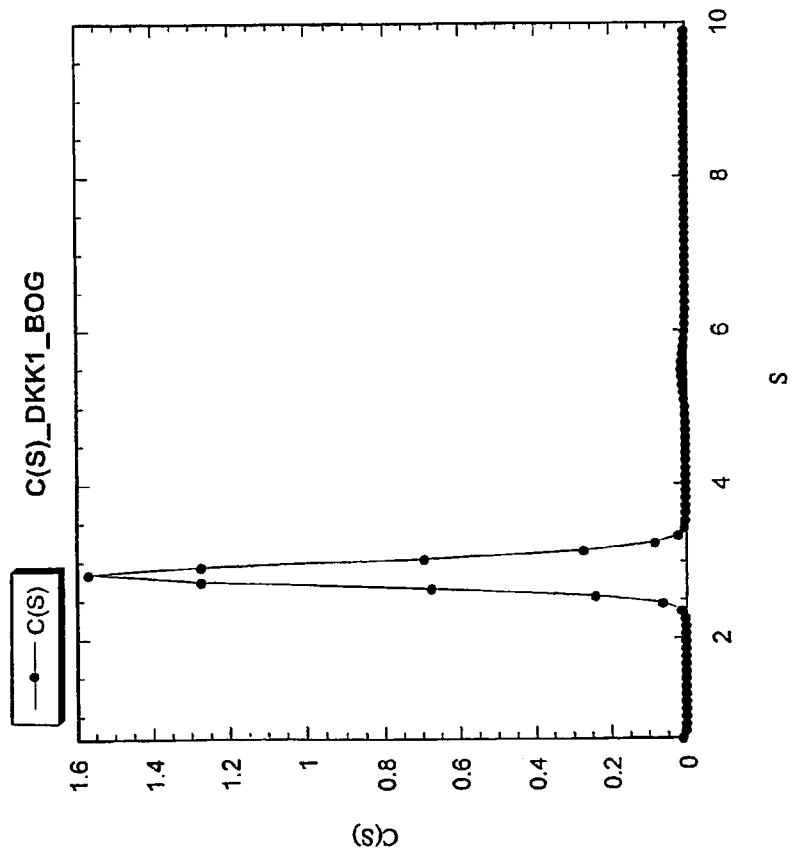
Figure 14D:
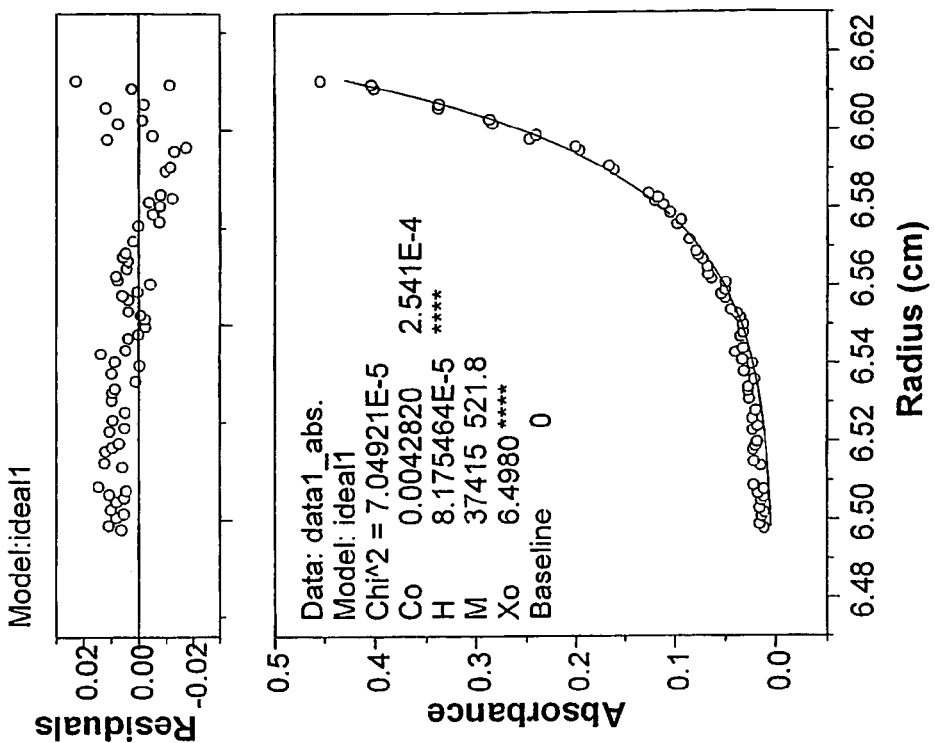
Figure 14C:
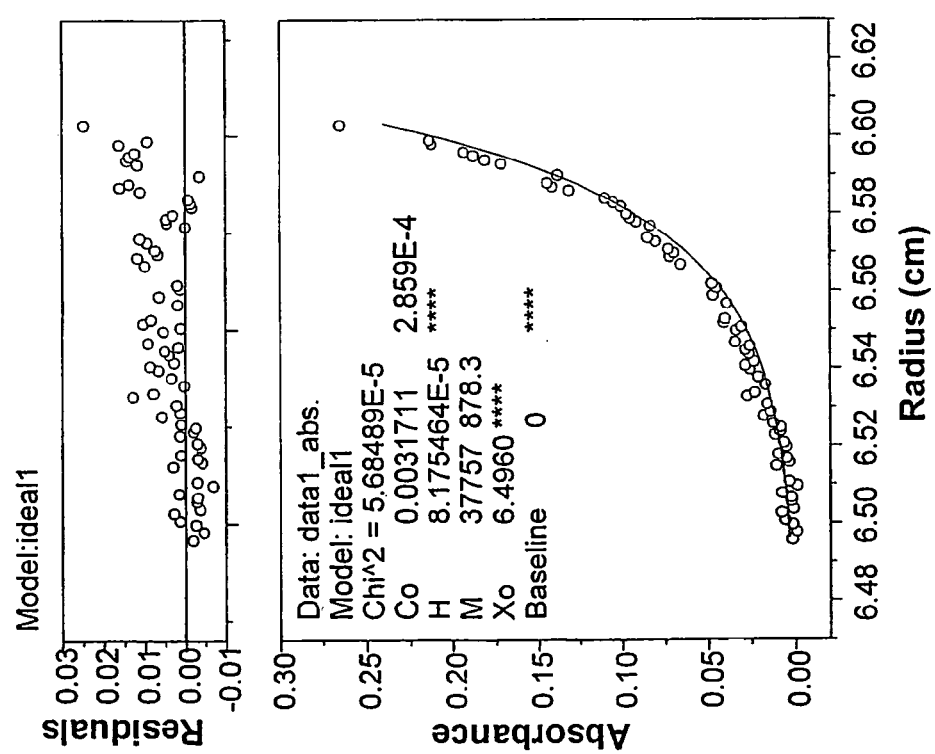

Dkk1 is glycosylated in the C-terminus. There is a 21-amino acid domain in the C-terminus which is important to glycosylation and Wnt3a-TCF signaling. The four members of the Dkk family of proteins contain two conserved cysteine rich domains separated by variable-length spacer regions. Dkk1 and Dkk2 are the most studied and share 50% homology at their N-terminal cysteine rich region and 70% homology at the C-terminal region (Glinka et al., 1998, *Nature* 391: 357-362; and Krupnick et al., 1999 *Gene* 238: 301-313). The importance of the conserved cysteine rich domains for Dkk1 activity has been demonstrated by point mutation of cysteine 220 to an alanine, C220A (Mao et al., 2001, *Nature* 411: 321-325). Accordingly 6 constructs were created to assess activity and roles of the various portions of Dkk1. FIG. 10 shows that only the wild-type Dkk1 can bind to both LBD1 and LBD4 of LRP5 in a yeast two hybrid (Y2H) assay and have Wnt-TCF inhibitor function in a TCF assay. The mutants wherein either the N-glycosylation domain and/or larger portions of the Dkk1 protein were deleted all resulted in loss of function with regard to one or more of the three listed activities. The mutant lacking the C-terminal 21-amino acids lost the TCF inhibition activity even though it still contained both cysteine rich domains. Even the C220A mutant, lacked the ability to bind to LRP5 at either the LBD1 or LBD4 sites and did not have any Wnt inhibitory function as measured in the Wnt TCF assay.

To obtain these results, six Dkk1 deletion constructs in the pcDNA3.1 vector were tested for activity along with a positive, wild-type control and the C220A mutant. The TCF-assay involves the co-transfection of a TCF reporter containing 16 copies of the Wnt-beta-catenin signal responsive TCF element, basal TK-promoter luciferase gene, TK-renilla as internal control, Wnt3a and various Dkk1 constructs into

| Source | Expression Level | Size/ Glycosylation | Activity in TCF Luciferase | Co-IP with LRP5 | Scalability |
|---|---|---|---|---|---|
| Drosophila (DES) | 0.1 µg/mL | 32 kD/short chains | Low | Not tested | No - expression Too low |
| Baculovirus (R&D Systems) | 10 µg/$300 | 32 kD/short chains | Low | No technical difficulties | No - high cost, low activity |
| Bacterial - renatured from inclusion bodies | 10 µg/mL | 29.5 kD/none | None | Not tested | No, high expression but no activity |
| Mammalian HEK293T transient cells | 5 µg/mL | 39 kD/long chains | Excellent | Excellent | Yes - high expression; high activity | human embryonic kidney 293A cells (HEK293 cells, ATCC) or into human osteosarcoma derived bone cells (U2OS, ATCC). The cells were cultured respectively in Dulbecco's minimum essential media (DMEM, Invitrogen) or RPMI (Invitrogen) supplemented with 10% heat inactivated fetal bovine serum, 1% glutamax (Invitrogen) and 1% penicillin/streptomycin (Invitrogen). HEK293A cells were plated at 40,000 cells per well and U2OS cells were plated at 25,000 cells per well of a 96-well plate. After 24 hours of incubation at 37° C. (cells were 80-90% confluent at that point), the media was replaced with 100 µL fresh serum free OPTIM media (Gibco/BRL). Both cell types were transfected with 16×TCF (TK)-firefly luciferase (0.3 µg/well), TK-renilla luciferase (0.06 µg/well) using LIPOFECTAMINE 2000® transfection Reagent OPromega, Madison, Wis.) pursuant to manufacturer's instructions. The DNA mix and reagent were then incubated for 30 minutes and 50 µL/well of the DNA-reagent mix was added to 100 µL of OPTIM and incubated for 4 hours at 37° C. The transfection medium was then replaced and 140 µL of fresh DMEM or RPMI media was added to the HEK293A and U2OS cells respectively. After 20-24 hours of incubation at 37° C. in a $CO_2$ incubator, the media was removed. The transfected cell monolayer was lysed using 150 µL of 1× lysis buffer of Dual Luci reagent (Promega Corp., Madison, Wis.). After 10 min., 20 µL of the lysate was transferred into a 96-well white plate (Packard/Costar). Cell lysates were mixed with 100 µL/well of LARII buffer (Dual Luci Reagent) and the Relative Luciferase Units (RLUs) were measured. This was followed by the addition of 100 µL/well of "stop & glo" reagent (Dual Luci reagent) and the internal control renilla luciferase was measured. The ratio of TCF-firefly luciferase to renilla was calculated and the activity is indicated in FIG. 10 as +/−.

Assessment of the mutants' ability to interact with LBD1 and LBD4 of LRP5 was assessed using a yeast two hybrid assay. The deletions showed that although binding with the LBD domains may remain as tested in the yeast two hybrid assay, the Dkk1 function was lost if the C-terminal 21 amino acids (i.e., N-RIQKDHHQASNSSRLHTCQRH-C) was missing when tested by the TCF assay.

Example 5

Inhibition of Wnt3a Activity by Dkk1

Another characteristic of the Dkk1 purified from HEK293T cells is its ability to inhibit Wnt3A mediated signaling. The purified HEK293T-derived Dkk1 was compared with Dkk1 from other sources to test the effect of purification method on Dkk1 activity.

The Dkk1 proteins used were as follows: 1) Recombinant human Dkk1 from R&D systems (Cat. No. 1096-DK/CF); 2) inclusion body Dkk1 solubilized in urea and renatured; 3) inclusion body Dkk1 solubilized in GuCl Dkk1 and renatured; 4) Dkk1 from conditioned media prepared from HEK293T cells transiently transfected with pcDNAmycHis-Dkk1—the wild-type gene; 5) Dkk1 from conditioned media prepared from HEK293T cells transiently transfected with pcDNAmycHisDkk1 C220A—a mutant form of the protein that prevents the binding of Dkk1 to LRP5, and therefore does not inhibit TCF luciferase activity.

The amount of Dkk1 in conditioned media was estimated by performing Western blots using a His antibody and comparing to purified Dkk1. After 20 hours, the cell lysates were assayed for luciferase activity (Promega Cat. No. E1960) as follows.

Preparation of frozen U2OS stock transfected with luciferase reporters. U2OS cells were seeded at $9.6 \times 10^6$ cells per T75 flask in McCoy's media supplemented with fetal calf serum (FCS). After culturing the cells for 16 hours (overnight) at 37° C., the cells were approximately 90% confluent. The cells were then transfected with 24 µg TCF-luciferase and 4.5 µg TK-renilla according to instructions by the manufacturer (Invitrogen). The transfected cells were then incubated at 37° C. for 24 hours. The media was removed and the cells trypsinized. Ten mLs of media was then added to the cells to stop the trypsinization process. The cells were collected and pelleted at 1,500 rpm for 5 minutes. The cells were then frozen at $10^6$ cells per mL per vial in McCoy's media supplemented with 10% FCS and 10% DMSO. Four T75 flasks yielded 24 frozen vials.

Treatment with Wnt3a and Dkk1 conditioned media. Frozen cells were thawed and plated at $2.5 \times 10^4$ cells per well on white Packard TM90 culture plates, followed by the addition of 100 µL/well of McCoy's media supplemented with 10% FCS. Wells from columns 1 and 12 were left empty. After the cells were incubated for 20 hours at 37° C., the media was aspirated off and 100 µL per well of conditioned media mixes were added. These consisted of 30 µL conditioned culture media from untransfected L cells (ATCC Cat. No. CRL-2648) or Wnt3A over-expressing L cells (ATCC Cat. No. CRL-2647) and HEK293/Dkk1mycHis conditioned culture media containing 2, 10, 25, 50 and 100 ng/well Dkk1. The cells were then incubated in the conditioned media at 37° C. for 20 hours.

A dual luciferase assay was performed utilizing Promega's Dual Luciferase Assay kit as follows. Media was aspirated from the cells. The cells were then washed 1× with 200 µL PBS. Cells were then lysed from the culture plate using 20 µL/well of lysis buffer. Cells were lysed using a gyratory shaker for at least 20 minutes at room temperature. 100 µL per well of LARII buffer was added to the lysed cells. Luminescence was read in cpm using a Wallac Victor V after 10 seconds of shaking followed by a 10 second delay. 100 µL per well of Stop & Glow buffer was added. Luminescence was again read using a Wallac Victor V after 10 seconds of shaking followed by a 10 second delay. The TCF/renilla ratio was calculated. The percent (%) inhibition is calculated by:

100−((TCF/Renilla with Dkk1)÷(TCF/Renilla without Dkk1))×100.

Figure 3:
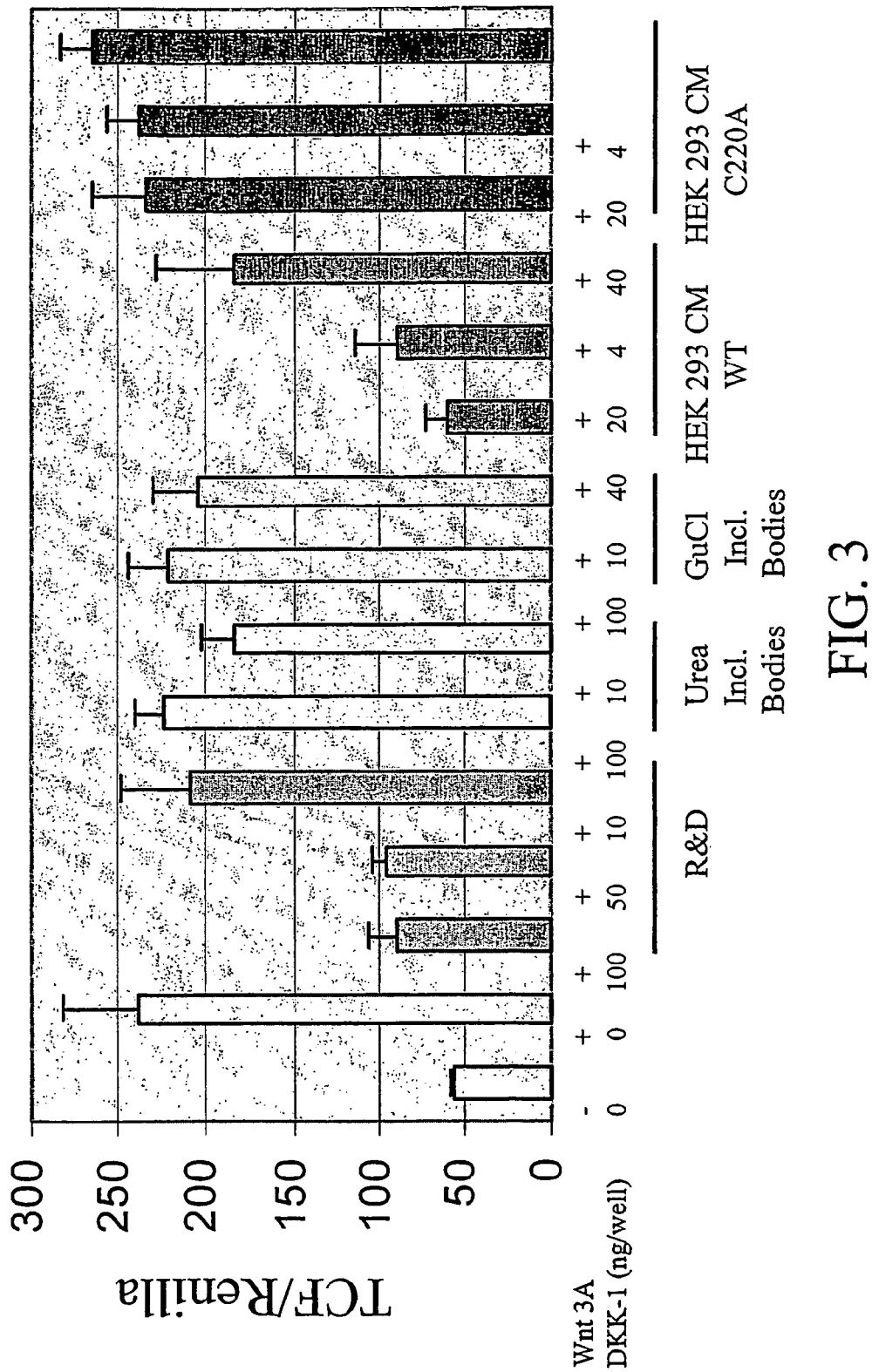
FIG. 3 Comparison of the inhibitory activity of various forms of Dkk1 protein on Wnt3a mediated signaling. By "Incl. Bodies" is meant inclusion bodies. The Dkk1 protein was isolated and purified from insoluble inclusion bodies using either urea or guanidine chloride (GuCl). Although the Dkk1 protein obtained from the insoluble inclusion bodies can be renatured through commercially available reagents or dialysis, it is not active in co-immunoprecipitation or TCF assays. By "C220A" is meant a Dkk1 variant wherein an alanine (A) is substituted for a cysteine (C) at amino acid position 220 in the Dkk1 polypeptide sequence. The amino acid substitution prevents the inhibition of Wnt mediated TCF activity and is thus a negative control since Dkk1 inhibits Wnt signaling. The variant is also tagged with a His tag. By "WT" is meant the wild-type Dkk1 with a His tag as expressed in HEK293T cells.

The data shown in FIG. 3 shows that baculovirus-derived Dkk1 (R&D Systems, Inc., Cat. No. 1096-DK/CF) was marginally active at a concentration of 50 ng/well. The Dkk1 obtained from bacterial inclusion bodies (i.e., "Incl. Bodies Urea" and "Incl. Bodies GuCl" wherein the Dkk1 was obtained by either urea or GuCl solubilization) had no activity, nor did the Dkk1 mutant negative control C220A have any activity. However, the Dkk1 obtained from HEK293T culture media was very active at 40 ng/well.

Example 6

Comparison of CM Dkk1 with Purified Dkk1

When proteins are purified, frequently the proteins lose some activity. Thus, an experiment was performed to compare the activity of the Dkk1 present in the culture media (CM) of the HEK293T cells versus the activity of the Dkk1 after it was purified from the culture media of the HEK293T cells. The activity was measured using a TCF luciferase assay as described above.

U2OS cells transiently transfected with luciferase reporters were treated with Wnt3A and Dkk1 as described for FIG.

Figure 4:
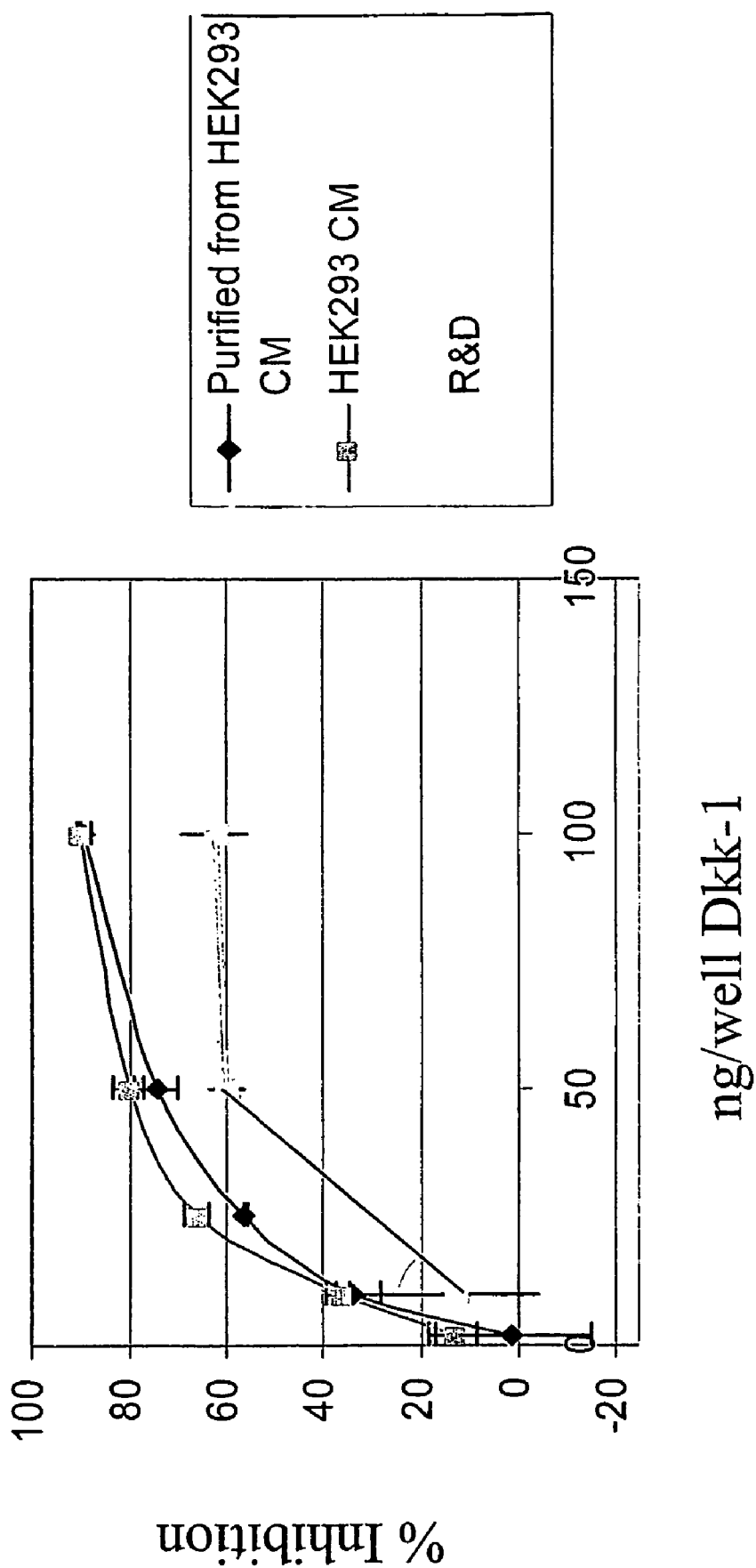
FIG. 4 Activity of purified Dkk1 in a TCF Assay. The activity of Dkk1 purified from HEK293T culture media (CM) (♦ in black), Dkk1 from HEK293T CM (unpurified; ■ in pink) and Dkk1 produced by R&D Systems (▲ in yellow) were assessed for activity using the TCF assay.

3 and the example supra. The Dkk1 isolated and purified from the HEK293T cell culture media (FIG. 4; ♦) had equivalent activity per ng as compared to the Dkk1 present in the culture media of the cells (unpurified; FIG. 4; ■). Therefore, the isolation and purification process from the culture media did not alter the activity of the protein.

The activity of these two sources of Dkk1 (purified and unpurified from HEK293T cell culture media; FIG. 4) was also compared to the commercially available baculovirus-derived Dkk1 (R&D Systems, Inc., Cat. No. 1096-DK/CF). Both the purified and unpurified ("CM") forms of Dkk1 from the HEK293T cells had significantly greater activity than the baculovirus Dkk1 (i.e., approximately 25% greater activity) when measured in the TCF luciferase assay (FIG. 4).

Example 7

Co-Immunoprecipitation of LRP5 with Dkk1

To further characterize the Dkk1 protein produced by HEK293T cells, a co-immunoprecipitation assay was performed to determine whether the Dkk1 can co-immunoprecipitate LRP5, and how such co-immunoprecipitation compares with Dkk1 proteins prepared by a different method or in non-mammalian cells.

After Dkk1 was purified as discussed in Examples 1-2 above, co-immunoprecipitation of Dkk1 and LRP5 was tested. First, Ultralink immobilized protein G (Pierce, Cat. No. 53125) was pre-blocked with culture media from untransfected HEK293T cells as follows. 100 μL of the bead suspension was microfuged for 30 seconds. The beads were then resuspended in 500 μL of culture media from untransfected HEK293T cells and incubated overnight at 4° C. with rotation.

The purified proteins or conditioned medias were then combined (see Table below) and incubated overnight at 4° C. with rotation. 100 μL of 0.5 M PIPES (pH 6 to 6.5) and 10 μL of 0.5% Tween-20 was added to each sample to a final concentration of 100 mM PIPES and 0.01% Tween-20, respectively.

The tubes were then spun in a microfuge at 4° C. for about 1 minute at 500 rpm. The supernatent was then carefully removed leaving the beads at the bottom of the tubes. The beads were washed with 1 mL 50 mM PIPES (pH 6 or 6.5) and 0.01% Tween-20 by flicking the tube. The resuspended beads were then incubated at 4° C. with rotation for 5 minutes. This step of washing and microfuging was performed an additional 3 times for a total of 4 washes with the 50 mM PIPES (pH 6 or 6.5) and 0.01% Tween-20. When the tubes were not being centrifuged they were kept on ice. After the final wash, Laemmli buffer was added to the beads and the samples boiled at 95° C. for about 3 to 5 minutes. The samples were then electrophoresed on a 12% SDS-PAGE gel as follows:

a. Samples were loaded onto a 12% SDS-PAGE gel (Bio-Rad Cat. No. 161-1156) along with 10 μL of rainbow marker (Amersham Cat. No. RPN 800). The 10× Tris/Glycine/SDS running buffer provided by Bio-Rad (Cat No. 161-0755) was diluted to 1× to make 1 L and used for the electrophoresis.

b. The SDS-PAGE gel was run at 100V for about 1 hr (until the dye reached the bottom of the gel). The gel was then electroblotted onto a membrane using the Mini Trans-Blot Electrophoretic Transfer Cell (Bio-Rad Cat No. 170-3930) as described by the manufacturer.

c. Transfer buffer (25 mM Tris, 192 nM glycine, and 20% methanol, pH 8.3) for transferring the proteins from the gel onto a membrane was prepared by mixing 3.03 g Tris (Trizma Base), 14.4 g glycine, and 200 mL of methanol (methanol); deionized and distilled $H_2O$ was added to a final volume of 1 liter).

d. Filter paper was cut to the size of the gel. The cut filter paper, fiber pad, and gel were briefly pre-soaked in transfer buffer for 2 minutes. Membrane, i.e. PVDF membrane (Bio-Rad, Cat No. 162-0182) was also cut to the size of gel (i.e., 6.5 cm by 8.5 cm). One corner of the blot was nicked and labeled as appropriate. The PVDF membrane was pre-wet by soaking in 100% methanol and then in transfer buffer.

| CM1 or Protein (V5) | Amount (μL) | CM2 (Myc) | Amount (μL) | OM (μL) | IP | Detect |
|---|---|---|---|---|---|---|
| Prop3, 4LBD CM | 300 | Dkk1 | 100 | 100 | Anti-Myc | Anti-V5 + Anti-Myc |
| Prop3, 4LBD protein | 3 (1 μg) | Dkk1 protein | 10 (1 μg) | 450 | Anti-Myc | Anti-V5 + Anti-Myc |
| ECD CM | 1,000 | Dkk1 | 100 | 0 | Anti-Myc | Anti-V5 + Anti-Myc |
| ECD protein | 50 (1 μg) | Dkk1 protein | 10 (1 μg) | 450 | Anti-Myc | Anti-V5 + Anti-Myc |

"ECD" = extracellular domain of LRP5 (amino acids 1 to 1376 corresponding to GenBank accession No. NP_002326)
"Prop3, 4LBD" = Propeller 3 and 4 and ligand binding domain of LRP5 (amino acids 642 to 1376 corresponding to GenBank accession No. NP_002326)
"OM" = OPTI-MEM (Invitrogen)
"CM" = conditioned media
"IP" = the antibody used in the precipitation
"Detect" = the antibody used for detection on the Western For immunoprecipitation, an anti-c-myc mouse monoclonal antibody (Rocile, Cat. No. 1667149) was used. To detect the bound antibody, HRP anti-V5 and HRP anti-myc (Invitrogen) were used. The next day, 50 μL of pre-blocked Ultralink immobilized protein G agarose and 2 μL of 1 μg/μL myc antibody in PBS (Roche, Cat. No. 1667149) was added to each microcentrifuge tube containing the mixed conditioned media. Samples were mixed by rotation at 4° C. for an additional 2 hours.

e. The electroblot "sandwich" was prepared according to the Bio-Rad Mini Trans-Blot Electrophoresis Transfer Cell protocol.

f. Proteins were transferred by electroblotting at 100 V for 1 hour at 4° C. as described by the manufacturer.

g. A blocking buffer (have to make fresh each time) was prepared as follows: 50 mL TBST buffer (20 mM Tris-HCl, pH 7.6, 137 mM NaCl, 0.1% Tween-20) plus 2.5 g non-fat dry milk (Bio-Rad, Cat No. 170-6404) and 0.5 g BSA. Fifty mL is sufficient for 2 membranes.

h. After transfer, the blot was rinsed with distilled and deionized H$_2$O briefly.

i. The membrane was then sealed in a bag containing 20 mL of blocking buffer and rocked at 4° C. overnight or for 1 hour at room temperature. Blots were rinsed 3 times, 5 minutes each in TBST with rocking at room temperature.

Proteins were detected on the blot using the HRP anti-V5 (Invitrogen, Cat. No. R961-25) and HRP anti-myc (Invitrogen, Cat No. R951-25) antibodies at a 1:5,000 dilution as follows:

a. The blot was incubated in 10 mL blocking buffer plus antibody with rocking at room temperature (RT) for 1 hour.

b. The blot was washed 4 times for 5 minutes each in TBST at RT with rocking.

c. The blot was drained on filter paper and placed protein side up on saran wrap.

d. ECL plus reagents (Amersham, Cat No. RPN 2132) were mixed and were pre-warmed to RT (5 mL A and 125 µL B) and pipetted evenly over the blot. The blot was incubated in these reagents for 5 minutes at RT.

e. The blot was drained on filter paper and wrapped in Saran wrap.

f. The membrane was taped protein side up. The blot was exposed to X-ray film for 15 seconds up to one hour depending on the exposure needed. Films were then processed through the developer.

Figure 5:
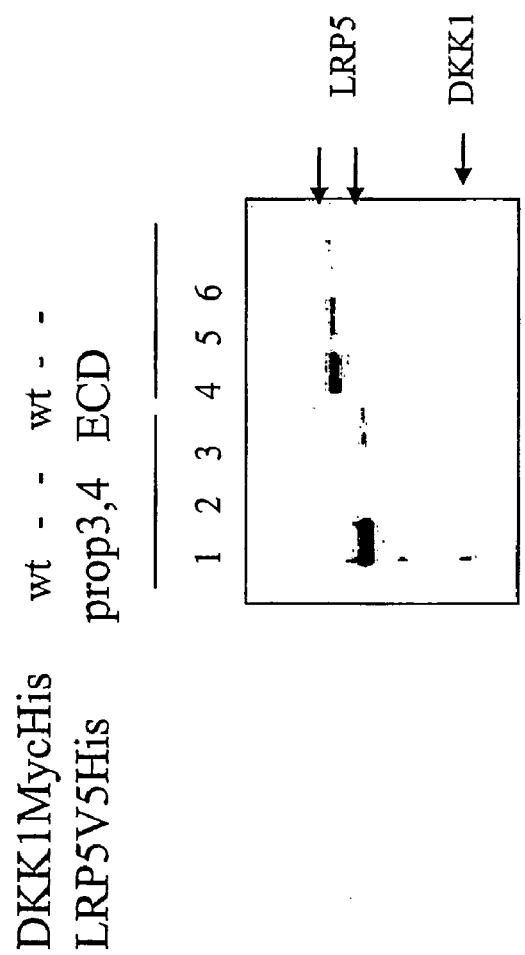
FIG. 5 Co-immunoprecipitation of LRP5 with Dkk1. Lanes 1-3 show the bands of LRP5VHis prop3,4 at about molecular weight 92 kD. Lanes 4-6 show the bands of LRP5Vhis ECD which migrates at a molecular weight of 158 kD. Lanes 1 and 4 were co-immunoprecipitated with wild-type Dkk1 (39 kD) obtained as described herein. Lanes 2, 3, 5 and 6 show the co-immunoprecipitation result in the absence of Dkk1.

The results obtained using these procedures are exemplified in FIG. 5. The Dkk1, purified as described above, is able to co-immunoprecipitate fragments of LRP5.

Example 8

Dkk1—LRP5prop34LBD Interactions

Dkk1 plays an important regulatory role in the Wnt pathway through its interaction with LRP5/LRP6. The genetic and molecular data indicate that the interaction between Dkk1 and LRP5 is critical for bone development. Thus, an assay to directly monitor the interaction between Dkk1 and LRP5, which can be used to screen for inhibitors of the Dkk-LRP5 interaction, was important to develop.

A fragment of LRP5, LRP5prop3,4LBD (amino acids 642 to 1376 from GenBank Accession No. NP_002326) is a part of the LRP5 extracellular domain that contains beta propellers 3 and 4 and the ligand binding domain (LBD). To test the interaction with this fragment, Dkk1 was purified from the conditioned media of HEK293T cells as described above. LRP5prop3,4LBD was purified from the conditioned media of HEK293T co-transfected with LRP5prop3,4LBD and Receptor-Associated Protein (RAP) expression vectors. RAP has been shown to function as a molecular chaperone in the endoplasmic reticulum that is required for proper folding and export of LRP5 (Hertz and Marschang, 2003 Cell 112: 289-292). Co-transfecting with this chaperone increases the yield of LRP5 secreted into the culture media. LRP5prop34LBD was cloned into the pcDNA3.1/V5 expression vector. RAP (GenBank Accession No. NP_002328) was cloned into the pCMVSport6 expression vector. LRP5prop34LBD was purified from conditioned media as described for Dkk1 above.

The time resolved fluorescence resonance energy transfer (TR-FRET) platform was chosen to develop an assay for Dkk1-LRP5prop34LBD interaction because the TR-FRET assay is highly sensitive, easy to set up and capable of detecting weak interactions. For this assay, two labeled molecules are added to the system. If an interaction occurs, the labels are brought into close proximity and energy transfer occurs to release energy at specific wavelengths that can be detected. For detection of interaction between Dkk1 and LRP5prop34LBD, the Dkk1 (tagged with myc) is effectively labeled using a Cy5 labeled monoclonal anti-myc antibody. The LRP5prop34LBD (tagged with V5) is effectively labeled using a Europium labeled monoclonal anti-V5 antibody. Europium is excited at 340 nm and re-emits energy at 615 nm. Cy5 absorbs at 615 nm and emits energy at 665 nm which is detected. The measurement was conducted on a Wallac EnVision 2100 Multilabel Reader from PerkinElmer Life Science. Emission at 665 nm is indicative of an interaction between Dkk1 and LRP5prop34LBD. The interaction between Dkk1 and LRP5prop3,4LBD is expressed as the ratio of fluorescence intensity at 665 nm over 615 nm, which represents the energy transfer from the europium to Cy5 dye. Cy5 labeled myc antibodies were purchased from Perkin-Elmer (AD0059). Europium labeled antibodies were generated following the protocols supplied by the manufacturer (Amersham Bioscience, Cat. No. PA99148).

Figure 6:
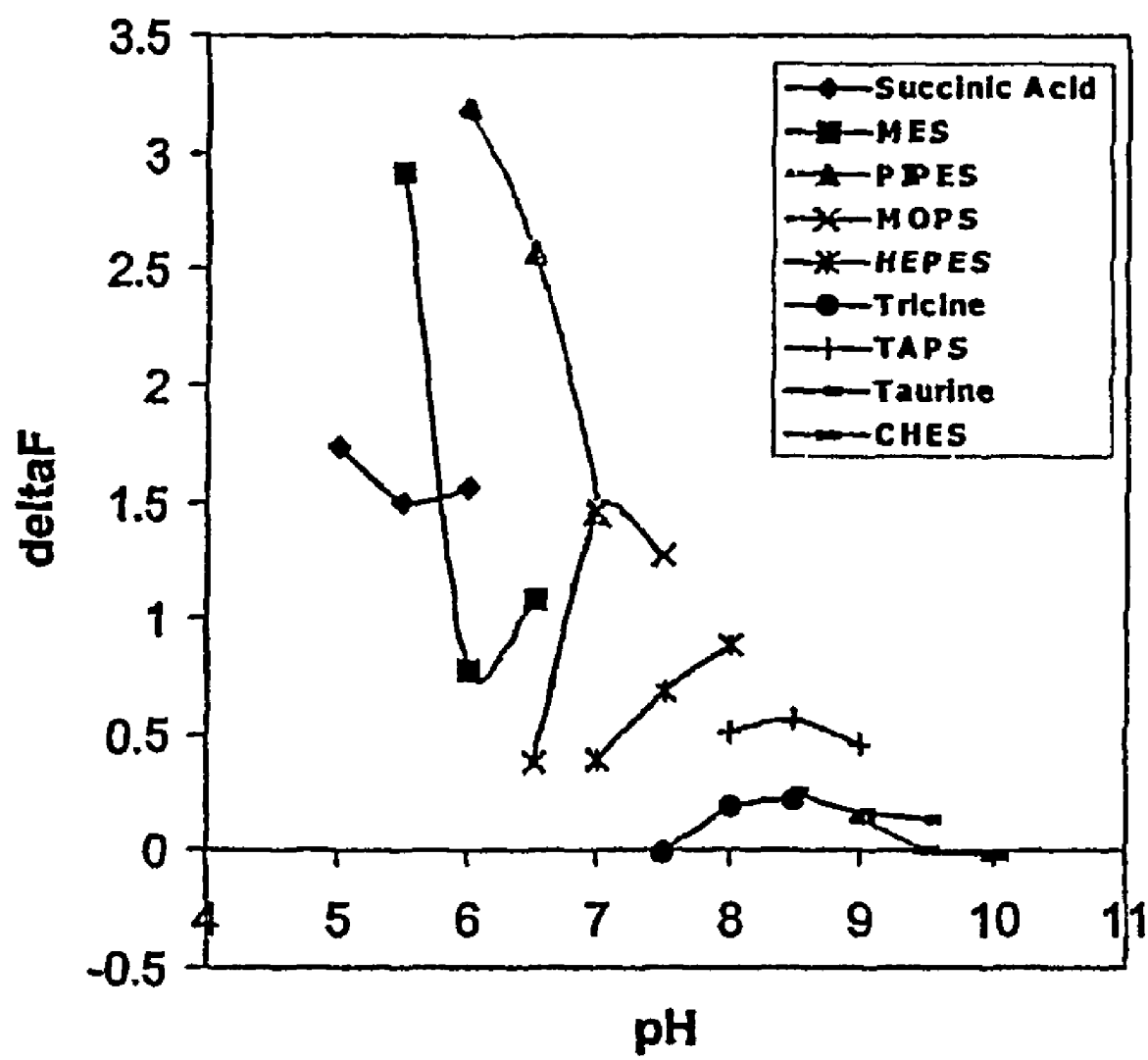
FIG. 6 Buffer selection for use in the Dkk1 and LRP5 fragment TR-FRET assay system. Succinic acid (♦), MES (■), PIPES (▲), MOPS (✖),HEPES (✱),tricine (●), TAPS (+), taurine (▬) and CHES (━)buffers were tested to select that buffer that produced the best signal to background ratio based on interaction of Dkk1 and LRP5prop3,4LBD.
Figure 7:
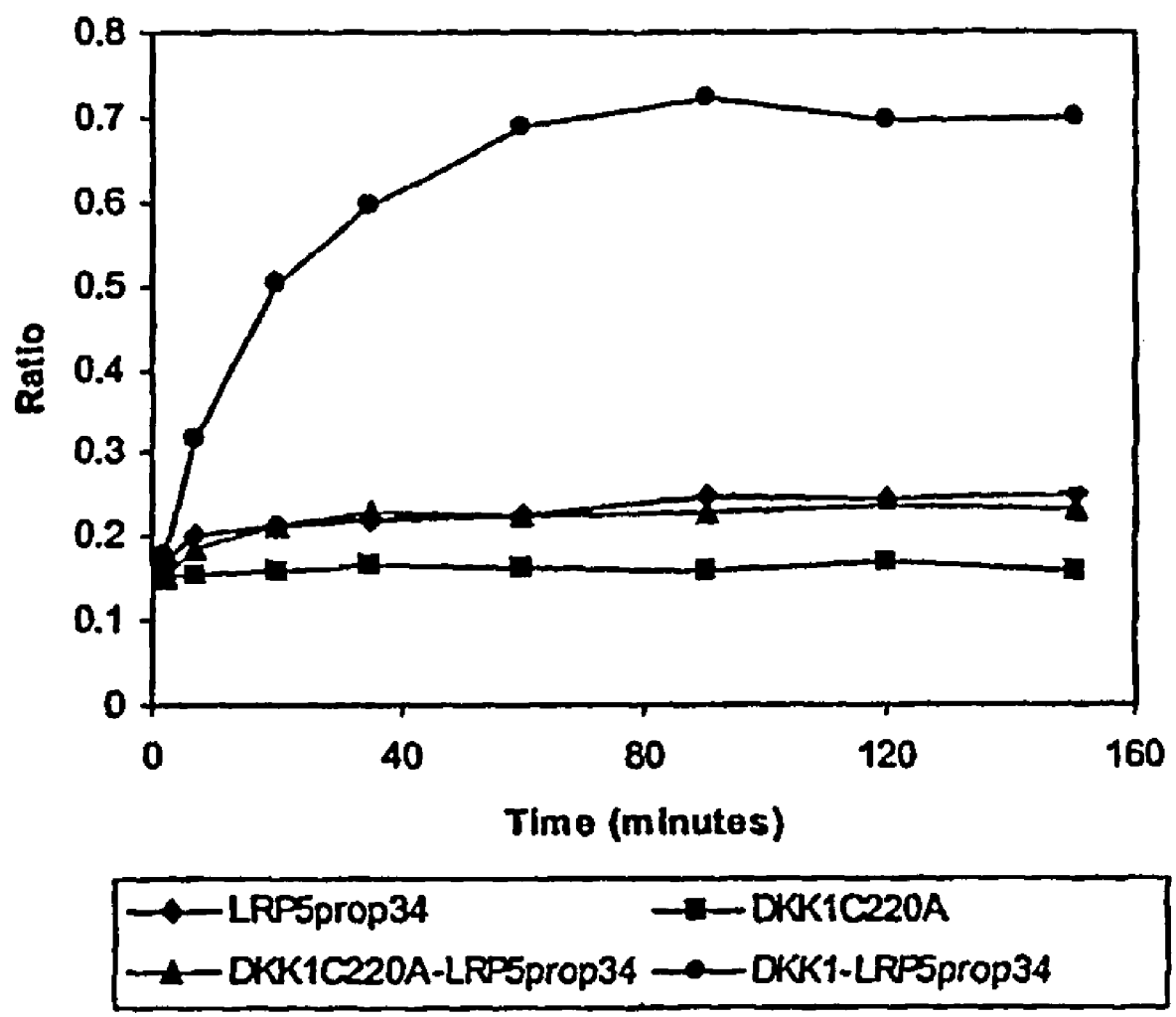
FIG. 7 Comparison of binding between Dkk1 and LRP5prop34 (●) as compared to Dkk1C220A (■), LRP5prop3,4 alone (♦) and Dkk1C220A-LRP5prop3,4 (▲).

Buffer Effect. In order to optimize the interaction between Dkk1 and LRP5prop34LBD, various buffers and pH's were tested under the following conditions:

50 mM various buffers at different pH's (see FIG. 6)
20 nM Dkk1
20 nM LRP5prop34LBD
0.5 nM V5-mAb-Eu
15 nM Myc-Ab-Cy5
0.01% Tween-20

The control was generated without LRP5prop34LBD using the same reaction mixture. Since different buffers generated different background signal, the result was shown as deltaF, where deltaF=((Sample−Control)÷Control). This value represents the signal/background ratio. The signal/background ratio of Dkk1-LRP5prop34LBD interaction detected with TR-FRET was highest in PIPES buffer. A pH of 6.5 was selected because it is closer to the physiological condition and yet still gives a reasonable signal/background ratio. The concentration of PIPES at pH 6.5 was then titrated. 50 mM was selected as optimal because the signal stopped increasing significantly as the PIPES concentration increased.

Salt Effect. Next, NaCl and CaCl$_2$ were tested to determine how they might affect the interaction between Dkk1 and LRP5prop34LBD. The detection system was not affected by NaCl and CaCl$_2$ at the concentration ranges tested. Reaction mixtures included 50 mM PIPES (pH 6.5), 20 nM Dkk1, 20 nM LRP5prop3,4LBD, 0.5 nM V5-mAb-Eu, 15 nM Myc-Ab-Cy5 and 0.01% Tween-20. Both NaCl and CaCl$_2$ were found to decrease the interaction between Dkk1 and LRP5prop34LBD. As a result, no salt is used in the reaction mixtures for the assay.

Reducing Reagent Effects. The effect of including reducing reagents in the assay was tested, as reducing reagents can decrease the false positives during compound analysis. DTT was found to increase the signal while at the same time also increasing the background. As DTT raised both values, 0.5 mM DTT used in the reaction mixture for further analyses. The reaction mixture after this test now included 50 mM PIPES (pH 6.5), 20 nM Dkk1, 20 nM LRP5prop3,4LBD, 0.5 nM V5-mAb-Eu, 15 nM Myc-Ab-Cy5, and 0.01% Tween-20.

DMSO Effect. Since many compounds are dissolved in DMSO, its presence can impact the interaction between Dkk1 and LRP5prop34LBD and thus its impact was tested. No significant effect was observed. Accordingly, the reaction mixture now included 50 mM PIPES (pH 6.5), 0.5 mM DTT, 20 nM Dkk1, 20 nM LRP5prop34LBD, 0.5 nM V5-mAb-Eu, 15 nM Myc-Ab-Cy5, and 0.01% Tween-20.

$K_{dapp}$ Determination. The observed $K_{dapp}$ was determined by varying concentrations of Dkk1 and LRP5prop34LBD in the reaction mixture containing 50 mM PIPES (pH 6.5), 0.5 mM DTT, 0.01% Tween-20, 0.5 nM V5-mAb-Eu, and 15 nM myc-Ab-Cy5. The TR-FRET data were obtained after equilibrium was achieved. After subtracting the background, the data were fitted using Grafit 5.0 software (Erithacus Software Ltd.). Under the conditions of described above, the $K_{dapp}$ was determined to be 11.81±2.26 nM. $K_d$-value determined here is a $K_{dapp}$-value as the antibody concentration is limiting in the assay. A true $K_d$-value could be determined with soluble Dkk1 and LRP5 using BIAcore, Differential Scanning Calorimetry, ITC, fluorescence (fluorescent labeling of the protein) and sedimentation equilibrium analyses.

Time course. The final assay conditions selected were 50 mM PIPES (pH 6.5), 0.5 mM DTT, 0.01% Tween-20, 5 nM Dkk1, 20 nM LRP5prop34LBD, 0.5 nM V5-mAb-Eu, and 10 nM Myc-Ab-Cy5. The reaction time for the assay was set at 90 minutes, which was the time period that achieved the peak interaction between Dkk1 and LRP5.

Assay Protocol. Based on the tests discussed above, the following Dkk1/LRP5 assay protocol was established:
1. Prepare assay plates containing compounds in wells from column 2 to column 11 leaving column 1 as a positive control and column 12 as the negative control, which contains the same solutions as that in which the compounds have been dissolved.
2. Prepare buffer comprising 50 mM PIPES (pH 6.5), 0.5 mM DTT and 0.01% Tween-20.
3. Prepare solution 1 containing 50 mM PIPES (pH 6.5), 0.5 mM DTT, 0.01% Tween-20 and 15 nM Dkk1.
4. Prepare solution 2 containing 50 mM PIPES (pH 6.5), 0.5 mM DTT, 0.01% Tween-20 and 60 nM LRP5prop34LBD.
5. Prepare Solution 3 containing 50 mM PIPES (pH 6.5), 0.5 nM DTT, 0.01% Tween-20, 1.5 nM V5-mAb-Eu, and 30 nM myc-Ab-Cy5.
6. To determine which compound interacts with the proteins, the following two experiments are carried out in parallel:
   (a) Pre-incubate compounds with Dkk1
      (i) Load 50 μL of solution 1 into wells from columns 1-11, and load 40 μL into column 12. Pre-incubate for 2 hours.
      (ii) Add 40 μL of solution 2 to wells from column 1-12.
   (b) Pre-incubate compounds with LRP5prop34LBD as follows:
      (i) Load 40 μL of solution 2 into wells from column 1 to 12. Pre-incubate for 2 hours.
      (ii) Add 40 μL of solution 1 to wells from columns 1-11 and load 40 μL buffer into column 12.
7. Add 40 μL of solution 3 to wells from column 1 to 12.
8. Incubate for 90 minutes at room temperature.
9. Read plates on Wallac EnVision 2100 Multilabel reader with setup as excitation at 340 nm, delay 60 μs, measurement window 100 μs, first emission at 665 nm and second emission at 615 nm.

Instrument and Setting. The measurements as discussed above were conducted using a Wallac EnVision 2100 Multi-label Reader from Perkin Elmer Life Science. Three required filters are: 340 nm with BW=60 nm, 665 nm with BW=7.5 nm and 615 nm with BW=8.5 nm, all of which were from Perkin Elmer. The instrument setting is excitation at 340 nm, first emission at 665 nm and second emission at 615 nm, delay time as 60 μs and measurement window time as 100 μs. The assay plate used was Costar 3694 EIA/RIA plate, 96 well, ½ area.

Figure 8:
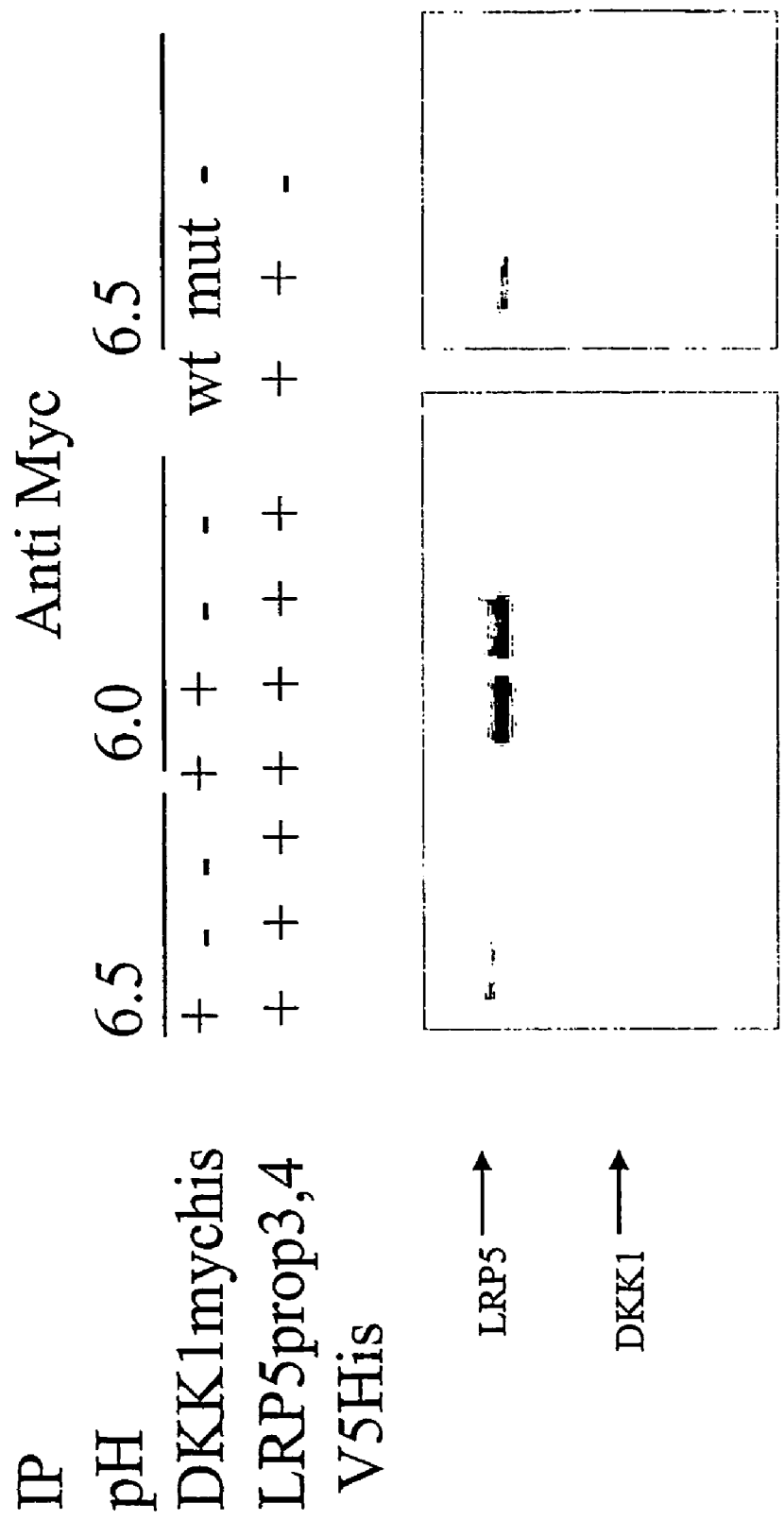
FIG. 8 Co-immunoprecipitation of Dkk1mycHis with LRP5prop34LBDV5His at either pH 6.5 or 6.0. By "mut" is meant the Dkk1C220A variant which cannot bind with LRP5.

Validation with mutated Dkk1 (Dkk1C220A). The purified Dkk1 mutant (Dkk1C220A) was tested under the same conditions to validate the assay since Dkk1C220A was not active in the TCF assay and does not co-immunoprecipitate LRP5-ECD (i.e., the extracellular domain of LRP5, amino acids 1 to 1376 corresponding to GenBank accession No. NP_002326). Dkk1C220A did not show any activity when tested using the TR-FRET assay discussed above. In order to confirm that the interaction between Dkk1 and LRP5prop34LBD could be detected reproducibly under the TR-FRET assay conditions, co-immunoprecipitation was performed under those exact assay conditions. The immunoprecipitation reaction was carried out as follows. The protein mixture, in this experiment conditioned media, in 50 mM PIPES (pH 6.5 or 6.0), 0.01% Tween-20 was incubated at 4° C. overnight. The protein complex was precipitated using an anti-myc mAb. The immunoprecipitate was then washed with the same buffer. Both antibodies against myc and V5 were used in the Western blotting. The mutant Dkk1 tested was Dkk1C220A. FIG. 8 shows that there is very low background when no Dkk1 is present, that the co-immunoprecipitation is more robust at pH 6.0 compared to 6.5 and that the mutant Dkk1 (C220A) fails to co-immunoprecipitate, as expected.

Example 9

Competitive Assay with Untagged Dkk1

Figure 9:
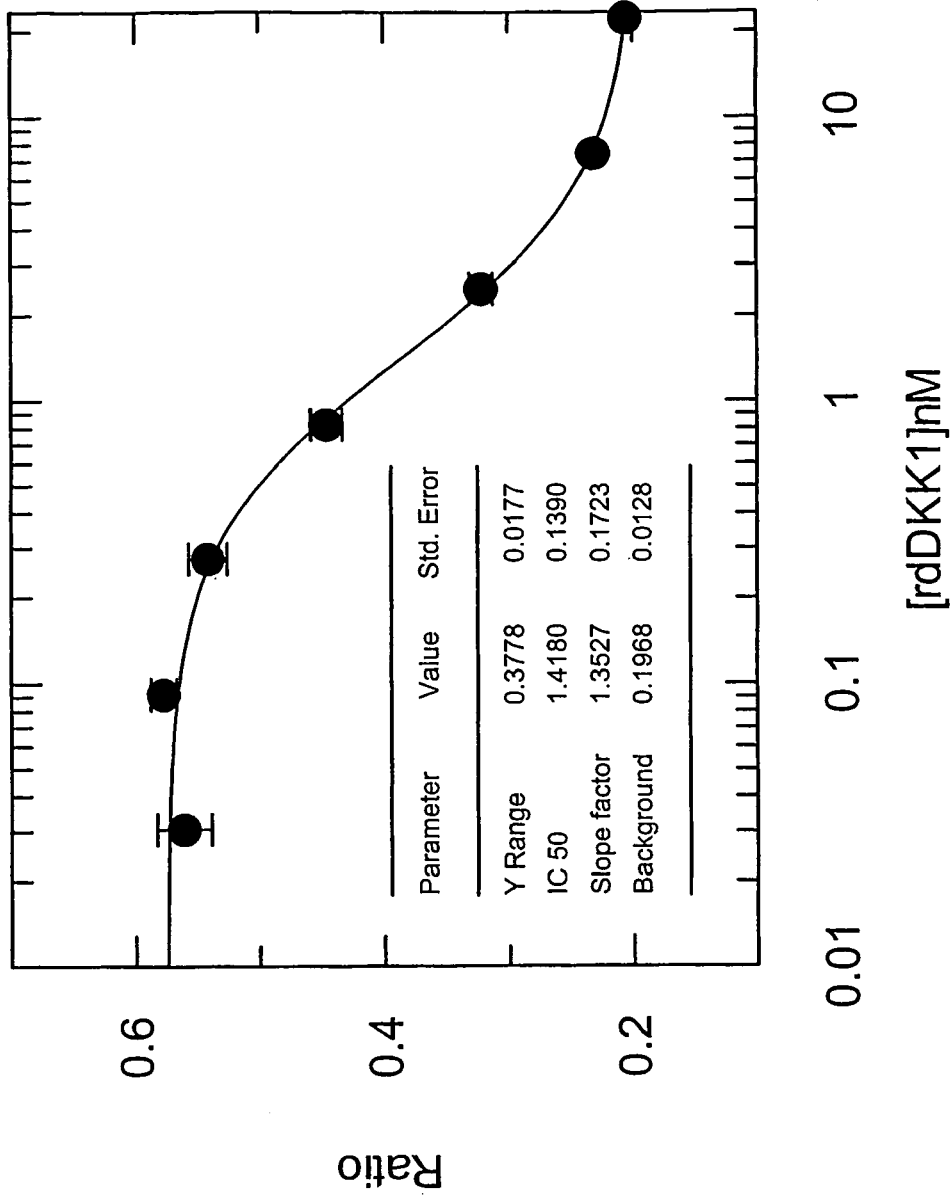
FIG. 9 Competitive assay with untagged Dkk1 from R&D systems.

Dkk1 without a myc tag was purchased from R&D Inc. and is a Dkk1 synthesized in a baculovirus/insect cell system. This form was used as a competitor to the Dkk1 tagged with myc. As shown in FIG. 9, R&D Dkk1 is a potent competitor with an $IC_{50}$ of 1.418 nM. Serial 3-fold dilutions of R&D Dkk1 were made in a 96-well assay plate starting at 12 μM in column 2 and ending at column 11 in a buffer containing 50 mM PIPES (pH 6.5), 0.5 mM DTT and 0.05% Tween-20. Column 1 and 12 were filled with 15 μl buffer (50 mM PIPES (pH 6.5), 0.5 mM DTT and 0.05% Tween-20). Two μl of R&D Dkk1 from each well in the dilution plate were transferred into an assay plate. The TR-FRET assay was then carried out as described above. The data were analyzed with Grafit 5 (Erithacus Software).

| Parameter | Value | Std. Error |
| --- | --- | --- |
| Y Range (665/615 fluor) | 0.3778 | 0.0177 |
| $IC_{50}$ (nM Dkk1) | 1.418 | 0.1390 |
| Slope Factor ((665/615)/nM Dkk1) | 1.3527 | 0.1723 |
| Background (665/615 fluor) | 0.1968 | 0.0128 |

Example 10

Use of Purified Human Dkk1 in a Radioligand Binding Assay

Purified Dkk1 (20 μg) was radiolabeled by Amersham Biosciences (Woburn, Mass.) with $^{125}I$ using a modification of the chloramine-T method (S. C. Greenwood et al., 1963, "The preparation of $^{131}I$-labelled human growth hormone of high specific activity," *Biochem. J.* 89: 114-123) and compared in a whole cell binding assay, modified from Bafico et al., *Nature Cell Biology* 3(7): 683-686 (2001), with recombinant human Dkk1 of R&D Systems. CHO-K1 cells that had been stably transfected with LRP5 (CHO 618.7 cells) were plated at 200,000 per well in 24-well plates one day prior to performing the assay. The cells were washed twice with assay buffer containing 1% BSA and then exposed to 0.4 nM of either the purified Dkk1 or recombinant (R & D systems) radioligand for 3 hours at room temperature (22° C.). Cells were then washed twice with PBS prior to lysing the cells with 0.5% SDS/PBS (100 µl). Lysates were then detected in a gamma counter.

The R&D Systems Dkk1 had a total binding of about 9800 and non-specific binding of about 5,000 as measured in counts (cpm). This was about 49% specific binding for R&D Dkk1. The purified Dkk-1 produced in the HEK293T cells had total binding of about 11,500 cpm and non-specific binding of about 4,300 cpm, giving about 63% specific binding for the purified Dkk-1 from HEK293T cells. When the same experiment was conducted again, R&D Dkk1 produced 32% specific binding and the purified Dkk1 of HEK293T cells produced about 49% specific binding. Thus, the wells using purified Dkk1 from HEK293T cells showed improved specific binding over the recombinant baculovirus produced Dkk1.

Example 11

Dkk1 Characterization by MS, SEC-MALLS and AUC

Mass spectroscopy (MS) analysis was performed to obtain a molecular weight of Dkk1 expressed in HEK293T cells. The molecular weight obtained by this method was 36.1 to 36.9 kD.

The molar mass and monodispersity of Dkk1 obtained from R&D Systems were compared with the Dkk1 produced and purified from HEK293T and HEK293 EBNA cells. This was performed using size exclusion chromatography coupled to multi-angle laser light scattering (SEC-MALLS).

The Dkk1 protein purified from HEK293T cells was solubilized in PBS with 0.1% Tween-20 and PBS. The Dkk1 protein of R&D systems was in Tris-Citrate buffer containing 500 mM NaCl. High protein concentrations rather than low amounts were used in the initial experiments because the oligomerization-state of Dkk1 is typically linked to protein concentration. Higher protein concentrations result in higher molar mass and dilution of protein typically tends to disaggregate the oligomers.

SEC-MALLS is an absolute method to determine molar mass of proteins in solution. The amount of light scattered is directly proportional to the product of the polymer molar mass and concentration. In this method, the light scattering signals are combined with the concentration detectors, UV and differential refractive index to obtain the molar mass of proteins. The Dkk1 protein was injected on a Biosep SEC 2000, and the molar mass distribution of each of the protein elution peaks was determined using the various light scattering and concentration detector signals. The resultant analyses of the data suggest that the Dkk1 purified from HEK293T cells exists as a mixture of trimers and tetramers, possibly in equilibrium in the original stock solution. Upon dilution, there is evidence for dissociation to predominantly the homodimer.

The resultant analyses of the data suggest that the Dkk1 purified from HEK293T cells exists as a mixture of trimers and tetramers, possibly in equilibrium. SEC-MALLS analyses in the presence of DTT did not alter the oligomerization state of the protein. This suggests that the oligomer formation is not linked to intermolecular disulfide bonds.

SEC-MALLS analysis of Dkk1 expressed in HEK293 EBNA cells was purified by $Ni^{2+}$ chromatography. It was observed that the baculovirus-derived Dkk1 protein from R&D Systems in the absence of detergent did not elute off the column. However, the Dkk1 protein derived from HEK293T cells eluted off the column, even in the absence of detergent in the running buffer.

The baculovirus-derived Dkk1 purchased from R&D Systems may be aggregated and/or extensive interactions with the column matrix may be occurring, which precluded elution of the Dkk1 protein off the column. The Dkk1 of R&D Systems does not have a detergent present, unlike the Dkk1 purified from HEK293T cells. Additionally, the Dkk1 of R&D systems is not glycosylated, whereas that purified from HEK293T cells is glycosylated. Both glycosylation and detergent may be required to maintain Dkk1 in a disaggregated state.

Dkk1 was analyzed by analytical ultracentrifugation utilizing both Sed-Vel. and Sed-Equil. techniques. Sed-Vel. was performed using a Beckman XL-I analytical ultracentrifuge using 2-sector cells. Sed-Vel. analysis showed that Dkk1 sediments as a uniform species with an S-value of 2.8S and a corresponding molecular mass of about 38 to about 42 kD. Sed-Equil. Analysis of Dkk1 was performed using a Beckman XL-I analytical ultracentrifuge using 6-sector cells. Dkk1 samples (100 µM stocks containing 0.1% Tween-20 or 0.7% N-BOG) were centrifuged at 3 concentrations (5, 1.55 and 0.5 µM respectively) and three speeds (25, 30, and 35 krpm respectively) until equilibrium was achieved. Each protein was diluted into PTS. The molecular mass of each protein was determined using Microcal Origin v. 3.78 and fitting the data to the Ideal 1 model.

Like the Sed-Vel. analysis, the data showed that Dkk1 behaves as a monomer with a molecular masses range from 36- to 46-kD. In this analysis, the oligomeric state is independent of the detergent used, detergent concentration, and protein concentration, possibly due to the long equilibration times of the protein. Summary of Dkk1 Molecular Mass Determinations from Hydrodynamic Analyses

| Method/Technique | Molecular Mass (kD) | Sed. Coefficient | Quaternary Structure |
|---|---|---|---|
| SEC-MALLS | ~74 | | dimer |
| Sed-Vel. | ~40 | 2.8 | monomer |
| Sed-Equil. | 36-46 | | monomer |

All cited patents and publications referred to in this application are herein incorporated by reference in their entirety for all purposes. International PCT Application PCT/US02/15982 and U.S. Ser. No. 10/182,936 are incorporated herein by reference in their entirety for all purposes. Applicants also incorporate herein by reference in its entirety for all purposes U.S. Provisional Application No. 60/555,406 filed Mar. 23, 2004.

We claim:

1. A method of concentrating an active, glycosylated Dkk protein, comprising:
    concentrating a culture media containing an active, glycosylated Dkk protein in the presence of EDTA and a detergent to obtain a concentrated Dkk protein, wherein the detergent does not inhibit the activity of the Dkk protein,
    wherein a mammalian host cell expresses the Dkk protein and secretes the Dkk protein into the culture media, and
    wherein the detergent is Tween-20 in the amount of about 0.01% to about 1% Tween-20, and EDTA is present in the amount of about 0.01 mM to about 2 mM EDTA.

2. The method of claim 1, wherein the yield of Dkk protein from the culture media is at least about 80%.

3. The method of claim 1, wherein the concentration of the active, glycosylated Dkk protein is at least about 2 mg/mL.

4. The method of claim 1, further comprising purifying the culture media across an affinity column prior to said concentrating.

5. The method of claim 1, further comprising purifying the Dkk protein by size-exclusion chromatography.

6. The method of claim 1, further comprising treating the culture media with one or more protease inhibitors.

7. The method of claim 1, further comprising the step of filtering the culture media prior to said concentrating.

8. The method of claim 4, wherein the affinity column is a metal affinity column.

9. The method of claim 5, wherein the size exclusion column is a Superose-12 column, a Superdex-200 column, a Sephacryl column, or a Sephadex column.

10. The method of claim 8, wherein the metal is nickel, zinc, or iron.

11. The method of claim 1, further comprising lyophilizing the purified, glycosylated Dkk protein.

12. The method of claim 1, wherein the Dkk protein is Dkk1.

13. The method of claim 12, wherein the Dkk1 protein is human Dkk1.

14. The method of claim 6, wherein said treating is performed in the presence of a salt and imidazole.

15. The method of claim 14, wherein the salt is NaCl, LiCl, or KCl, and wherein the salt is in a final concentration of about 100 mM to about 1 M, and the imidazole is present in a final concentration of about 0.5 mM to about 50 mM.

16. The method of claim 14, wherein the salt is NaCl and is present at a final concentration of about 500 mM, and the imidazole is present at a final concentration of about 5 mM.

17. The method of claim 8, wherein the metal affinity column is eluted with an imidazole gradient of about 5 to about 1,500 mM imidazole, and wherein the Dkk protein is tagged with histidine.

18. The method of claim 17, wherein the imidazole gradient is about a 20 mM to about a 1,000 mM imidazole.

19. The method of claim 17, wherein the Dkk protein is human Dkk1, and the metal affinity column is a nickel affinity column.

20. The method of claim 1, wherein the mammalian host cell is a HEK293T or HEK293 EPNA cell.

* * * * *